US012778411B2

(12) United States Patent
Sebag et al.

(10) Patent No.: US 12,778,411 B2
(45) Date of Patent: Nov. 3, 2026

(54) OPTOMETRY DEVICE FOR TESTING AN INDIVIDUAL'S EYE, SET OF PICTURES FOR SAID DEVICE AND DISPLAY UNIT OF SUCH SET OF PICTURES

(71) Applicant: Essilor International, Charenton-le-Pont (FR)

(72) Inventors: Mathilde Sebag, Charenton-le-Pont (FR); Adèle Longo, Charenton-le-Pont (FR); Juliette Papin, Charenton-le-Pont (FR); Mechtilde Nouvellon, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 446 days.

(21) Appl. No.: 18/250,031

(22) PCT Filed: Oct. 21, 2021

(86) PCT No.: PCT/EP2021/079245

§ 371 (c)(1),
(2) Date: Apr. 21, 2023

(87) PCT Pub. No.: WO2022/084460

PCT Pub. Date: Apr. 28, 2022

(65) Prior Publication Data

US 2023/0404387 A1 Dec. 21, 2023

(51) Int. Cl.
*A61B 3/032* (2006.01)
*A61B 3/04* (2006.01)

(52) U.S. Cl.
CPC ................ *A61B 3/032* (2013.01); *A61B 3/04* (2013.01)

(58) Field of Classification Search
CPC ....... A61B 3/032; A61B 3/0041; A61B 3/103; A61B 3/0008; A61B 3/063; A61B 3/022;
(Continued)

(56) References Cited

U.S. PATENT DOCUMENTS 8,419,184 B1 * 4/2013 Butler .................. A61B 3/0285 351/205
10,152,898 B2 * 12/2018 Rhea ........................ G09B 5/02
(Continued)

FOREIGN PATENT DOCUMENTS

CN 105764405 A 7/2016
CN 105916432 A 8/2016
(Continued)

OTHER PUBLICATIONS

Office Action issued Feb. 5, 2026, in Chinese Patent Application No. 202180072027.X, with English translation.
(Continued)

*Primary Examiner* — Sharrief I Broome
*Assistant Examiner* — Journey F Sumlar
(74) *Attorney, Agent, or Firm* — Oblon, McClelland, Maier & Neustadt, L.L.P.

(57) ABSTRACT

An optometry device for testing an individual's eye, including a refraction test unit having a vision correction optical system for providing different vision correction power values, and a display unit comprising a control unit controlling a projection optical system adapted to produce from a scene picture and from a visual test picture including a functional zone, respectively, along a scene optical path of the projection optical system, a scene image at a scene distance from the individual's eye, and along a visual test optical path of the projection optical system, a visual test image at a visual test distance from the individual's eye smaller than or equal to the scene distance of projection, the visual test image being superimposed at least partially with the scene image.

13 Claims, 9 Drawing Sheets

(58) Field of Classification Search
CPC ..... A61B 3/08; A61B 2560/0223; A61B 3/02; A61B 3/028; A61B 3/0285; A61B 3/09; A61B 3/005; A61B 3/0058; A61B 3/0075; A61B 3/0091
See application file for complete search history.

(56) References Cited

U.S. PATENT DOCUMENTS

| | | | | |
|---|---|---|---|---|
| 2008/0259277 | A1 | 10/2008 | Inagaki et al. | |
| 2009/0086166 | A1 * | 4/2009 | Kanazawa | A61B 3/08 351/240 |
| 2014/0211164 | A1 * | 7/2014 | Nakamura | A61B 3/032 351/239 |
| 2015/0160539 | A1 * | 6/2015 | Bassi | G03B 21/147 353/69 |
| 2016/0302710 | A1 * | 10/2016 | Alberts | A61B 5/1125 |
| 2017/0164822 | A1 | 6/2017 | Kalder et al. | |
| 2017/0311796 | A1 * | 11/2017 | Walsh | A61B 3/0058 |
| 2018/0116500 | A1 * | 5/2018 | Escalier | A61B 3/02 |
| 2018/0249151 | A1 * | 8/2018 | Freeman | G16H 40/63 |
| 2019/0274539 | A1 | 9/2019 | Nauche et al. | |
| 2020/0015672 | A1 * | 1/2020 | Nauche | A61B 3/0008 |
| 2020/0046220 | A1 | 2/2020 | Tatara | |
| 2020/0272232 | A1 * | 8/2020 | Lussier | G02B 27/0025 |

FOREIGN PATENT DOCUMENTS

| | | | | |
|---|---|---|---|---|
| CN | 109788896 | A | 5/2019 | |
| CN | 111712179 | A | 9/2020 | |
| EP | 1 982 642 | A1 | 10/2008 | |
| EP | 3 298 952 | A1 | 3/2018 | |
| EP | 3 329 837 | A1 | 6/2018 | |
| EP | 3 607 871 | A1 | 2/2020 | |
| KR | 102031580 | B1 * | 11/2019 | G09G 3/3406 |
| WO | WO 2015/107303 | A1 | 7/2015 | |
| WO | WO 2015/155458 | A1 | 10/2015 | |

OTHER PUBLICATIONS

International Search Report mailed on Jan. 5, 2022 in PCT/EP2021/079245 filed on Oct. 21, 2021, (6 pages).

Office Action issued May 6, 2026, in Korean Patent Application No. 10-2023-7013510, with English translation.

* cited by examiner

Fig.16
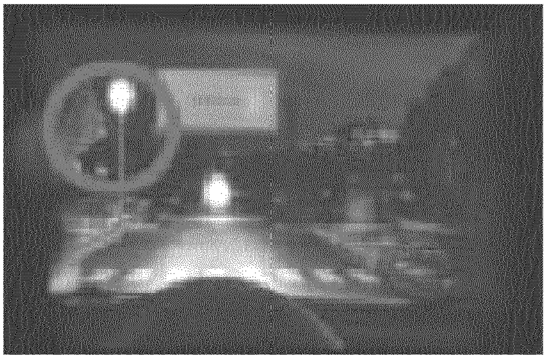
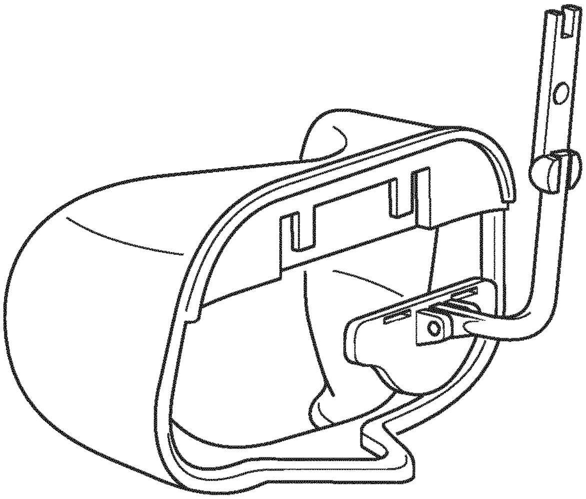
Fig.17a
Fig.17b
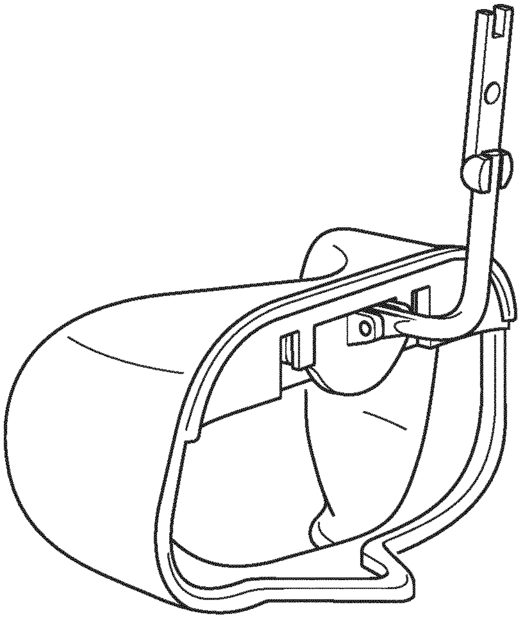

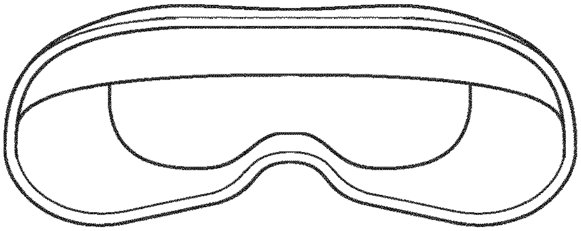
Fig.18
Fig.19
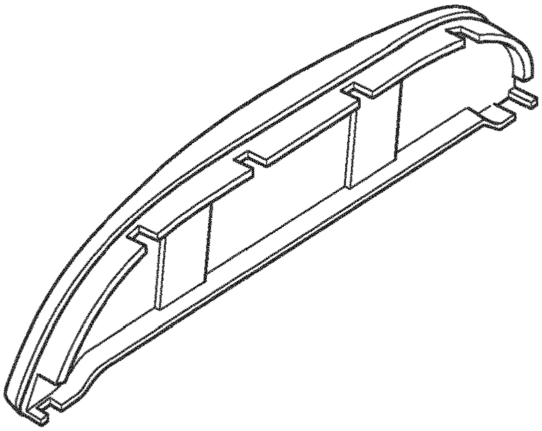
Fig.20a
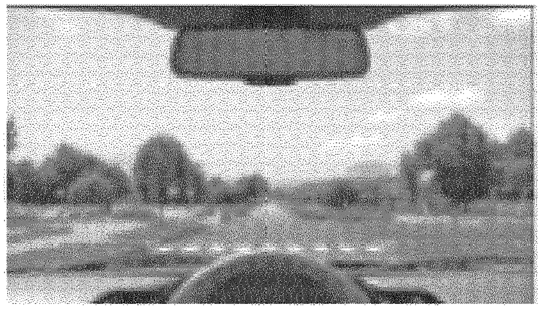
Fig.20b
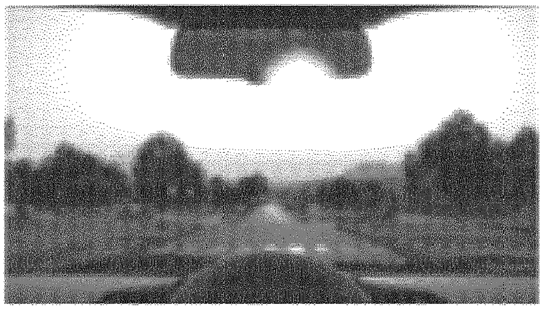
Fig.20c
Fig.20d
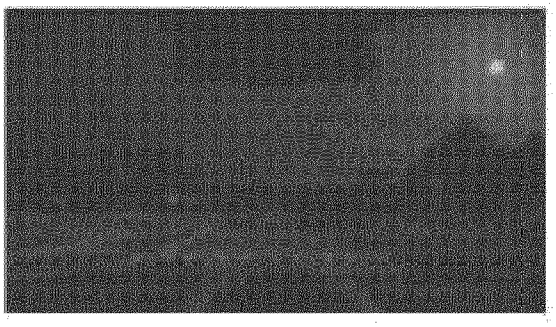

OPTOMETRY DEVICE FOR TESTING AN INDIVIDUAL'S EYE, SET OF PICTURES FOR SAID DEVICE AND DISPLAY UNIT OF SUCH SET OF PICTURES

TECHNICAL FIELD OF THE INVENTION

The invention relates to an optometry device for testing an individual's eye, to a set of pictures for said device and to a display unit of such set of pictures.

BACKGROUND INFORMATION AND PRIOR ART

Document EP 3 298 952 describes such a device comprising:

a refraction test unit having a vision correction optical system for providing different vision correction power values; and a display unit comprising:

a projection optical system adapted to produce from a scene picture and from a visual test picture including a functional zone, respectively:

a scene image produced along a scene optical path of said projection optical system at a scene distance from the individual's eye; and a visual test image produced along a visual test optical path of said projection optical system at a visual test distance from the individual's eye, said visual test image being superimposed at least partially with said scene image; and at least one control unit adapted to control said projection optical system.

In this device, the contrast of the visual test image seen by the individual through the refraction test unit may be low due to the superimposition of the scene image with the visual test image.

Hence, this device with said display unit may not exhibit the same reliability and the same precision as a standard device for measuring the subjective refraction of an individual.

SUMMARY OF THE INVENTION

Therefore one object of the invention is to provide an optometry device for measuring the subjective refraction of an individual that delivers measurement results which can be compared to those of a standard device.

The above objects are achieved according to the invention by providing an optometry device as defined above, wherein said at least one control unit is configured to define in the scene picture at least one scene zone implying transparency for the corresponding virtual scene image and in the superimposition area between the visual test image and the scene image, allowing the individual's eye to observe the functional zone of the visual test image without contrast decrease, at the visual test distance.

It is thus possible with the invention to enhance the contrast of the visual test image perceived by the individual looking both at the visual test image and at the scene image at the same time through the refraction test unit.

Other advantageous and non-limiting features of the optometry device according to the invention include:

said at least one scene zone implying transparency is configured by the control unit to have a predetermined colorimetry distribution compared to the remaining parts of said scene picture;

said predetermined colorimetry distribution of the at least one scene zone implying transparency is configured by the control unit to have a luminance lower than 100 cd/$m^2$, preferably lower than 50 cd/$m^2$, more preferably lower than cd/$m^2$;

the at least one control unit drives the projection optical system so that a peripheral zone of said scene zone implying transparency is fuzzy;

said scene zone implying transparency has a relative position in the scene picture which depends on the tested individual's eye and on the visual test distance of projection;

the scene zone implying transparency has a shape and an aspect ratio substantially identical to a shape and aspect ratio of the visual test image as defined at the visual test distance from the individual's eye and a size which is larger than a size of the visual test image as defined at the visual test distance from the individual's eye, preferably 5 to 33% larger, even more preferably between 10 to 20% larger;

said visual test distance of projection is modifiable, and said visual test image dimensions changes in function of visual test distance, said at least one control unit being configured to modify the dimensions of the at least one scene zone implying transparency according to the dimensions of the visual test image;

said visual test distance of projection is modifiable and said at least one control unit is configured to define in the visual test picture one frame implying transparency for the corresponding virtual visual test image, surrounding the functional zone of the visual test picture, the frame shape features being modified based on said visual test distance so as the functional zone of the visual test image to have a shape and an aspect ratio substantially identical for different visual test distances;

said at least one control unit is configured to define for the functional zone of the visual test picture a background with a high luminance and optotypes with lower luminance, the difference between the luminances of the background and of the optotypes being superior or equal to 2% in order to define for the corresponding picture, dark optotypes positioned in a bright background;

said at least one control unit is configured to define in the functional zone of the visual test picture a background with a low luminance and optotypes with higher luminance, the difference between the luminances of the optotypes and of the background being superior or equal to 2%, the control unit being configured to define in the visual test picture in addition a positioning frame surrounding the functional zone and of a higher luminance than background of the functional zone, in order to define for the corresponding picture a bright positioning frame for the bright optotypes positioned in a dark background, the difference between the luminances of the positioning frame and of the background being superior or equal to 2%;

the visual test distance of projection is modifiable and the at least one control unit drives the projection optical system to produce a visual test picture whose color temperature and/or luminance depends on the visual test distances of projection for the visual test image in order to provide for the corresponding visual test images produced with varying visual test distances, a constant color temperature and/or luminance;

said projection optical system is arranged so that said scene distance of projection is fixed.

The invention also relates to a set of pictures comprising a visual test picture and a scene picture, said set of pictures being useful for an optometry device having a vision correction optical system for providing different vision correction power values for testing an individual's eye, the optometry device including a projection optical system adapted to produce from corresponding scene picture and corresponding visual test picture including a functional zone, respectively:

- a scene image produced along a scene optical path of said projection optical system at a scene distance from the individual's eye; and
- a visual test image produced along a visual test optical path of said projection optical system at a visual test distance from the individual's eye smaller than or equal to said scene distance of projection, being superimposed at least partially with the scene image.

Other advantageous and non-limiting features of the set of pictures according to the invention include:

- the scene picture comprises at least one scene zone implying transparency for the corresponding virtual scene image and in the superimposition area between the visual test image and the scene image allowing the individual's eye to observe the functional zone of the visual test image without contrast decrease at the visual test distance;
- the scene picture comprises at least two opposed bottom vanishing lines oriented in the direction of the scene zone implying transparency, defining background areas and foreground areas along the vanishing lines, and wherein the functional zone of the visual test picture is defined such that the functional zone appears on the visual test image as being displayed in a vertical plane for the individual;
- said visual test distance is modifiable at least between a far and a near test distance, and wherein the vanishing lines converge toward a point positioned below the zone implying transparency for far test distance, and above or into said zone implying transparency for near test distance;
- the different areas along the vanishing lines defining different blur levels comprise a horizon area dedicated to define for the corresponding scene image, the farthest background for the observer that is defined with the maximal level of blur;
- said visual test distance is modifiable at least between a far and a near test distance, wherein the scene picture is modifiable between a corresponding far scene picture and a corresponding near scene picture, the smaller level of blur of the far scene picture being defined in an area coinciding with the end of the vanishing line and with the zone implying transparency, the smaller level of blur of the near scene picture being defined in an area coinciding with the beginning of the vanishing line and with the zone implying transparency;
- the scene picture comprises several elements at the periphery of the opposed vanishing lines acting as distance perception clues;
- the several elements are identical in shape and with decreasing sizes along the vanishing line in direction of the zone implying transparency;
- some of the several elements are different in shape and in size and superimposed one on another;
- said visual test distance is modifiable and the visual test image has a size defining an angle of view that is larger for shorter visual test distance and smaller for longer visual test distance, and the zone implying transparency of the scene picture has a shape and aspect ratio substantially identical to a shape and an aspect ratio of the visual test image observed for the considered visual test distance;
- the functional zone of the visual test picture comprises a background with a texture and/or colorimetry distribution chosen in function of a corresponding texture and/or colorimetry distribution of an area of the scene picture surrounding the zone implying transparency;
- the visual test picture comprises several symbols different in shape, in size, in contrast level, in spatial frequency, in texture, in orientation, in kind among letters, symbols, numbers, pictograms, and/or in relative contrast among standard contrast (bright symbol on dark background) and reverse contrast (dark symbol on bright background);
- the set of pictures comprises several visual test pictures and several corresponding scene pictures intended to be displayed successively so as to define a video;
- the sequence of successive visual test pictures and corresponding scene pictures defines colorimetry and/or luminance evolution so as to provide an observer of the corresponding sequence of images, with a perception of the light conditions changing between dark to bright conditions;
- as preferred, the control unit controls the scene and the visual test pictures to have a corresponding colorimetry distribution defining a combined image with a predetermined luminance level;
- ideally, the predetermined luminance level is set by the control unit to be lower than 100 cd/m$^2$, preferably lower than 50 cd/m$^2$, more preferably lower than cd/m$^2$, even more preferably below 10 cd/m$^2$;
- according to an additional embodiment of the invention, said predetermined colorimetry distribution of the at least one scene zone implying transparency is configured by the control unit to have a color in the RGB color model whose each component is below 40, more preferably below 30, more preferably below 20, more preferably below 10, more preferably below 5 and more preferably equal to zero, out of 255;
- ideally, the projection optical system comprises a visual test screen and a scene screen each defining a main face and controlled by the control unit to display through their main faces respectively the visual test picture and the scene picture and to constitute a combined image resulting from the superimposition of the visual test image at least partially with said scene image the control unit controlling dependently the colorimetry distributions of the scene picture displayed by the scene screen and of the visual test image displayed by the acuity screen to display a combined image uniform in colorimetry distribution along an observation optical path of said projection optical system;
- according to another interesting embodiment, the optometry device comprises inside a casing including the display unit, a light source controlled by the control unit, the control unit controlling dependently the colorimetry distributions of the scene picture, of the visual test image and the ones of the light source, to display a combined image uniform in colorimetry distribution along the observation optical path of said projection optical system;
- as a preference, at least one anti-reflective coating is provided on the main face(s) of the visual test screen and/or the scene screen;

as a preference, the optometry device comprises light isolating device protruding from a front main face of the refraction test unit and aiming at isolating from the light environment the individual's eye;

more precisely, the light isolating device includes a flexible mask aiming at conforming with at least part of the subject's face and surrounding the subject's eyes, and a rigid junction part connecting the flexible mask to a head support of the refraction test unit;

ideally the junction part is made by additive manufacturing.

The invention further concerns a computer-program product for a data processing device, the computer program product comprising a set of instructions which, when loaded into the data processing device, causes the data processing device to perform the display of the set of images as defined above.

Finally, the invention relates to a display unit comprising:

a projection optical system adapted to produce from a scene picture and from a visual test picture including a functional zone, respectively:

a scene image produced along a scene optical path of said projection optical system at a scene distance from the individual's eye; and a visual test image produced along a visual test optical path of said projection optical system at a visual test distance from the individual's eye, being superimposed at least partially with the scene image; and at least one control unit adapted to control said projection optical system and including the computer-program product defined above, the control unit including a data processing device.

DETAILED DESCRIPTION OF EXAMPLE(S)

The following description, enriched with joint drawings that should be taken as non limitative examples, will help understand the invention and figure out how it can be realized.

FIG. 16 shows a combined image resulting from the virtual merge of the scene image and the visual test image with dependent colorimetry distributions as controlled by the control unit to define a night driving light condition, FIGS. 17*a* and 17*b* illustrate a light isolating device including a flexible mask aiming at conforming with at least part of the subject's face and surrounding the subject's eyes, and a rigid junction part connecting the flexible mask to a head support of the refraction test unit, in an disengaged (FIG. 17*a*) and in an engaged (FIG. 17*b*) configurations, FIG. 18 is a 3D view of the flexible mask of the FIG. 18, FIG. 19 is a perspective view of the rigid junction part of the light isolating device of the FIGS. 17*a* and 17*b,*

FIGS. 20*a*-20*d* are images displaying light condition evolution between day (FIG. 20*a*) and night (FIG. 20*d*) through dust (FIG. 20*b*) and dark (FIG. 20*c*).

In the following description, identical or corresponding elements of each embodiment will be referred to with the same sign of reference and will not be described in details each time.

The optical paths of light are represented in dashed lines, the sense of propagation of the light being indicated by arrowheads.

The visual sensation of a color stimulus is generally considered as being separated into two supposedly independent parts, luminance and chromaticity.

Luminance is the power of visible light passing or being emitted at a surface element in a given direction, per unit area and per unit of solid angle.

Mobility of an optical component is indicated by double arrows placed beside.

Figure 1:
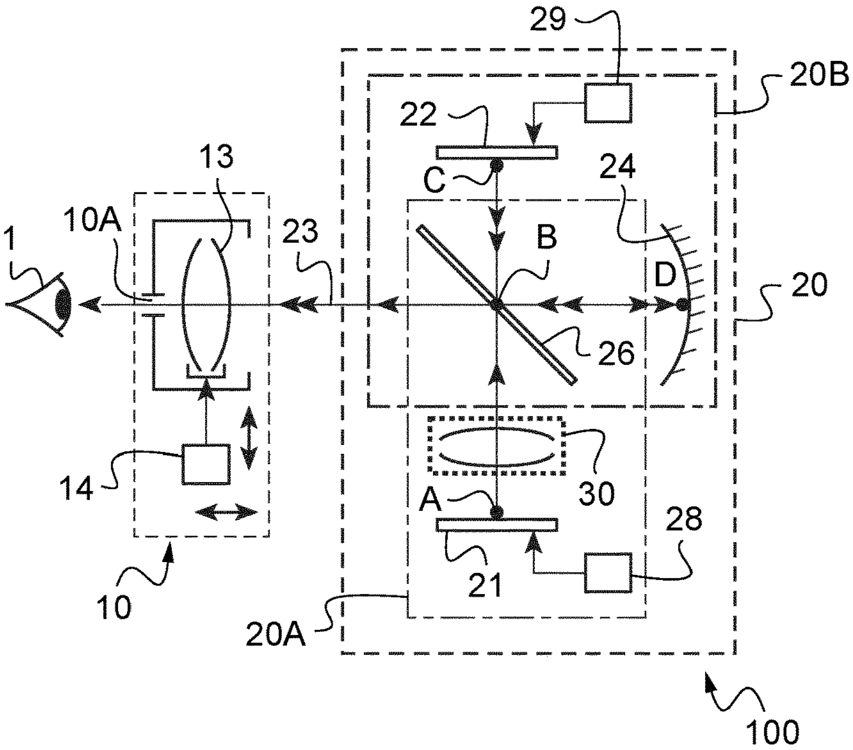
FIG. 1 represents a schematic view of the optometry device according to the invention.
Figure 2:
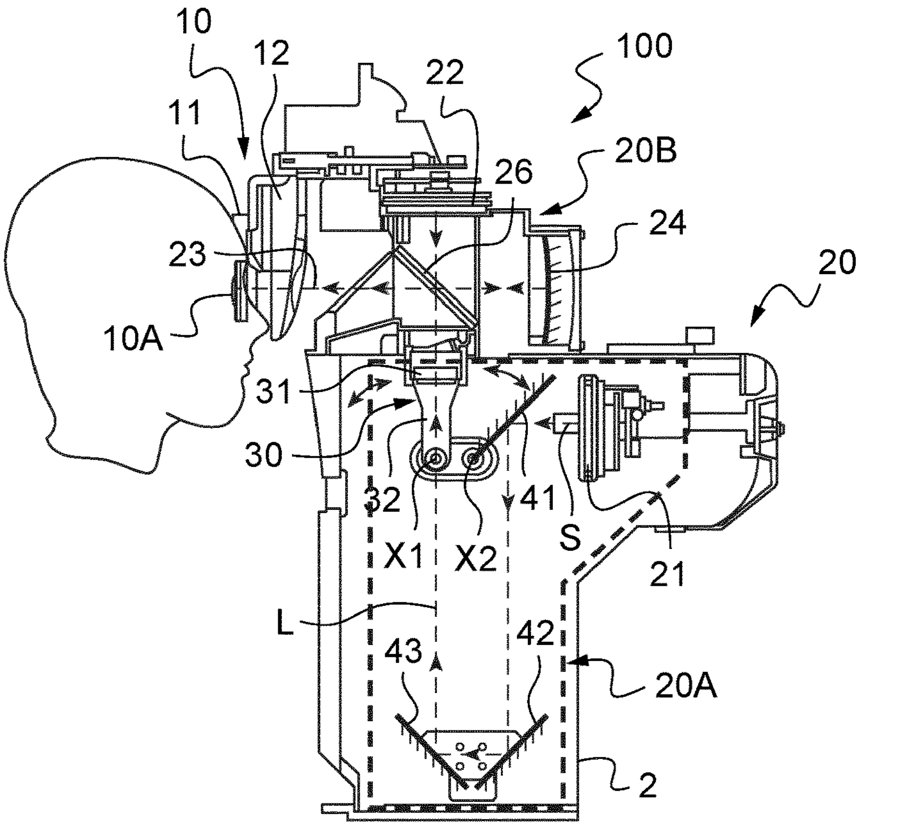
FIGS. 2 and 3 show a possible embodiment of the optometry device of FIG. 1 in two different configurations.
Figure 3:
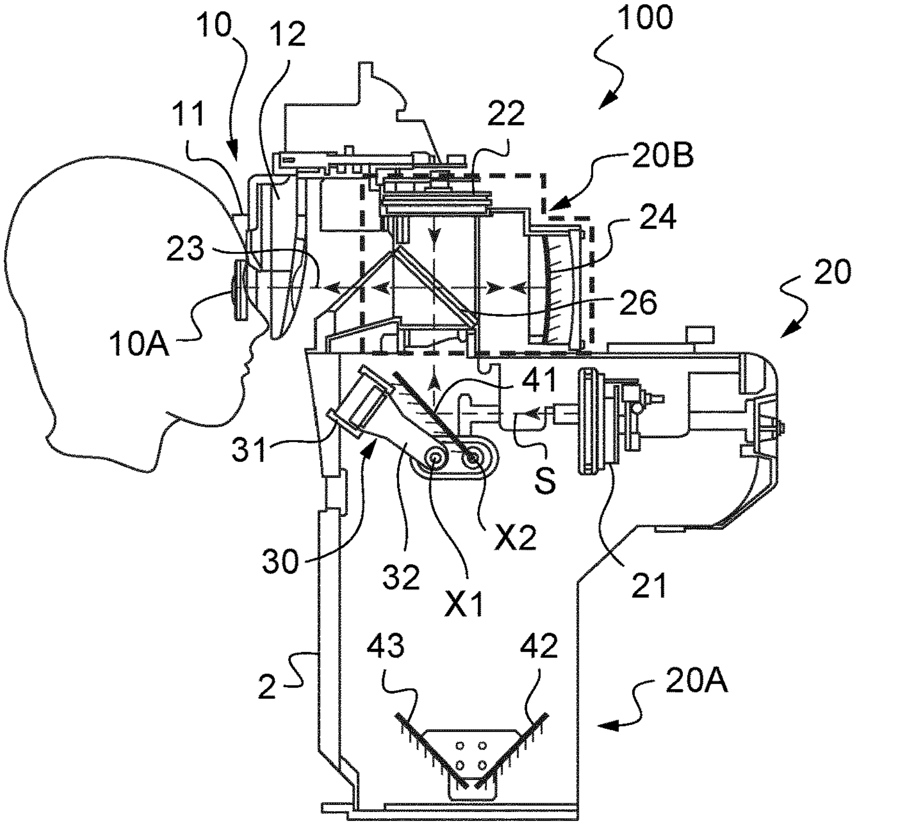

We represent on FIGS. 1-3 an optometry device 100 for testing an individual's eye 1 (see FIG. 1) according to the invention.

The optometry device 100 comprises:

a refraction test unit 10 having a vision correction optical system 13 for providing different vision correction power values close to both eyes 1 of the individual, equipped with two movable refraction heads mounted mobile between a closed configuration wherein said two heads are positioned in front of the two eyes of the individual, and an opened configuration (not shown), wherein said two head are positioned away from the eyes of the individual, and a display unit 20 adapted to produce both a visual test image and a scene image for the individual's eye 1.

In the present embodiment represented on the FIGS. 1-3, the optometry device 100 also includes a casing 2 adapted to be placed for example on a table, for instance, or to be mounted on a stand to be placed on a table or on the floor.

The casing 2 encloses here the display unit 20 whereas the refraction test unit 10 of the optometry device 100 is here mounted on the casing 2, at the exterior of the latter.

The visual test image and the scene image are visible by the individual through the vision correction optical system 13 of the refraction test unit 10 when the refraction heads adopt their closed configuration (we will explain later how those images are formed) or without this vision correction optical system 13 when the refraction heads adopt their opened configuration. In practice, the visual test image and the scene image are visible through an exit aperture 10A of the refraction test unit 10 of the optometry device 100.

The refraction test unit 10 is interposed between the display unit 20 and the individual's eye 1 in the closed configuration of the refraction heads. It is movable (see double-heads arrow in FIG. 1) so that its position may be adjusted in front of the eyes 1 of the individual.

The refraction test unit 10 may be of any kind known to the man skilled in the art. Such refraction test unit 10 is usually called "phoropter". A phoropter is adapted to provide a variable optical correction for the individual's eye 1 looking through it.

In particular, it may comprise a classical optical system 13 (see FIG. 1) for presenting different lenses with different optical powers in front of one or each eye 1 of the individual, or no lens or a blank lens with no optical power.

The lenses with different powers are interchanged through a manual or preferably through a motorized command (not represented). These different powers are vision correction powers for the eye 1 of the individual placed nearby.

The refraction test unit 10 preferably comprises a vision correction optical system with one or a plurality of lenses with adjustable power, such as liquid lenses.

The refraction test unit 10 is for instance a visual compensation system as described in document WO 2015/155458.

The refraction test unit 10 for example includes a lens having a variable spherical power.

Said variable spherical power lens has for instance a deformable surface. The shape of this surface (in particular the radius of curvature of this surface, and hence the spherical power provided by the lens) can be controlled by moving a mechanical part (such as a ring), which mechanical part may be driven by a motor of the refraction test unit 10.

The refraction test unit may also include a pair of independently rotatable lenses each having a cylindrical power. These lenses may each be rotated by action of other motors of the refraction test unit 10.

The various motors of the refraction test unit 10 are driven by a control unit 14 (e.g. see FIG. 1) such that the combination of the variable spherical power lens and the two cylindrical power lenses provides a desired spherical correction and a desired cylindrical correction (cylindrical power and cylindrical axes) to the individual's eye 1, as explained in document WO 2015/107303.

The various elements of the refraction test unit 10 (such as the variable spherical power lens, the cylindrical lenses, the motors and the control unit) are enclosed in a housing 12 shown on FIGS. 2 and 3.

In the present embodiment, the optometry device 100 includes two visual compensation systems as mentioned above (vision correction optical system), each such system being situated in front of one of the individual's eyes. The adjustable powers of these visual compensation systems are vision correction powers for the eye 1 of the individual placed nearby.

The exit aperture 10A of the optometry device 100 corresponds to opening of the refraction test unit 10 where the individual may position his eye 1 to look through the optical system 13 of the refraction test unit 10, namely the phoropter or visual compensation system (vision correction optical system). This exit aperture is centered on the optical axis of the lens or lenses of the refraction test unit.

However, the exit aperture is usually off-centered relative to an optical axis of the optical elements of the display unit, as will be described in more details later.

The refraction test unit 10 optionally comprises one or more elements designed to receive the head 13 (see FIGS. 2-3) of the individual and hold it in a predetermined position relative to the refraction test unit 10, and hence to the exit aperture 10A. This element may for example receive the forehead of the individual, such as element 11 represented on the FIGS. 2 and 3.

Alternatively or in addition, the refraction test unit could comprise an element to receive the chin of the individual.

Such refraction test unit 10 is well-known in the art of optometry and will not be described in more details here.

In the closed configuration of the refraction heads, the light beam 23 (see FIG. 1) exiting the display unit 20 is directed through the lens or lenses 13 of the refraction test unit 10 towards the eye 1 of the individual. The eye 1 of the individual is applied against the exit aperture 10A (or each eye of the individual is applied against a respective exit aperture) of the refraction test unit 10, through which the light beam 23 emitted by the first screen 21 and the second screen 22 (see below) exits the optometry device 100. In the opened configuration of the refraction heads, the light beam is directed towards the eyes of the individual at the exit of the optometry device.

In the invention, and as represented on FIG. 1, the display unit 20 comprises a projection optical system 25, 27 and at least one control unit 28, 29 adapted to control this projection optical system 25, 27.

In the example of FIG. 1, the projection optical unit comprises:

- a first projection sub-system 20A or "acuity module" controlled by a first (or acuity) control unit 28; and
- a second projection sub-system 20B or "scene module" controlled by a second (or scene) control unit 29.

Hence, the projection optical system can produce simultaneously two kinds of images.

First, the first projection sub-system 20A (i.e. "acuity module") forms (i.e. projects) a visual test image OPT (see FIG. 4) along a visual test optical path of the first projection sub-system 25, this first optical path going (see simple arrows on FIG. 1) here from point A (on first screen 21) to point B and then after reflection on the semi-reflective plate 26 to the eye 1 of the individual through the exit aperture 10A of the phoropter 10.

Optically, the visual test image OPT is visible by the individual through the vision correction optical system 13 at a visual test distance (hereinafter noted D1) from the individual's eye 1.

In the example of FIG. 1, the visual test image is a virtual image formed by the projection optical system (and more precisely by the first projection sub-system 20A) which projects a visual test picture (not visible in FIG. 1) displayed on a visual test screen 21 (first screen) and by an optical element 30 (if present as explained later), that optically transforms said visual test picture into the virtual visual test image.

Second, the second projection sub-system 20B (i.e. "scene module") forms (i.e. projects) a scene image SCN (see FIG. 4) all along a background optical path of the projection sub-system 20B, this second optical path going (see double arrows on FIG. 1) here from point C (on second screen 22) to point B and to point D (on mirror 24), and from this point D to point B, and after transmission through the semi-reflective plate 26 (which is communal to both projection sub-systems 20A, to the eye 1 of the individual.

Like the respective optical paths described above, the scene image SCN is superimposed with the visual test image OPT and is visible by the individual through the vision correction optical system 13 at a background distance of projection (hereinafter noted D2) from the individual's eye 1. In practice, this background distance D2 of projection is greater than or equal to the visual test distance D1 of projection.

Again, in the example of FIG. 1, the scene image is a virtual image formed by the projection optical system (and more precisely by the second projection sub-system 20B or "scene module") which projects a background picture (not visible in FIG. 1) displayed on a scene screen 22 (or second screen) and by the optical element 30 (if present as explained later), that optically transforms said scene picture into the virtual scene image.

The visual test screen 21 and the scene screen 22 are any kind of flat panel displays such as a TFT-LCD screen or an OLED/QLED/μLED screen.

We will now describe in more details the example of acuity module 20A with reference to FIGS. 2 and 3.

As shown on these figures, the acuity module 20A comprises at least one optical element 30 having an optical power (in diopters).

This optical element 30 is movable between:

- a first or "active" position in which it is placed on the visual test optical path of the light emitted by the visual test screen 21 and exiting the device 100 through the exit aperture 10A of the refraction test unit 10; and
- a second or "retracted" position in which it remains out of the visual test optical path, in order for the visual test image to be produced (i.e. optically formed) at a variable distance from the exit aperture 10A.

The visual optical path is the path that a light beam emitted by the visual test screen 21 at a center of the picture displayed by this screen 21 takes in traversing the display unit 20 to reach the exit aperture 10A of the refraction test unit 10.

Hence, the visual test image OPT comprises:

- an image of the visual test picture displayed on the first screen 21 without influence of the optical element 30, and reflected or not by a reflecting surface of the device 100; or
- an image of this visual test picture displayed on the first screen 21 and projected by the optical element 30, reflected or not by a reflecting surface of the device 100.

By "projected", it is meant that an image of the visual test picture is optically formed by the optical element, such as e.g. the lens 31. This optical image of the visual test picture formed by the lens (and reflected or not) is a virtual image of the visual test picture displayed on the first screen 21.

When the optical element 30 is in its retracted position (e.g. see FIG. 3), the visual test image OPT comprises the (image of the) visual test picture (in this case, image magnification=1) displayed by said screen 21. The distance D1 between the visual test image OPT and the exit aperture 10A of the refraction test unit 10 is then the distance measured along the visual test optical path between the exit aperture 10A and the acuity screen 21 (including the optical folding paths defined by the reflecting surface if present).

When the optical element 30 is in its active position (e.g. see FIG. 2), the visual test image comprises an image (or projection) of the visual test picture displayed by the screen 21 seen by the individual through the optical element 30. This optical image is usually a virtual image. It is located at an optical position which may, for example, be at infinity (from the eye 1 of the individual).

The distance D1 of projection between the visual test image OPT and the exit aperture 10A of the refraction test unit 10 is then the geometrical/physical distance between the exit aperture 10A (which is generally planar or substantially planar) and the optical position of the (virtual) visual test image (including the optical folding paths defined by the reflecting surface if present).

The optical element 30 may comprise for example an optical lens 31, as in the example described here (see FIGS. 2 and 3).

In the case where the optical element 30 comprises an optical lens 31, the image of the visual test picture is the image of the visual test picture seen through the lens 31.

In the present optometry device 100, the distance D1 between the visual test image OPT and the exit aperture 10A can vary at least between a distance of far vision (FV) and a different distance of near (NV) or intermediate vision (IV).

A distance of far vision is typically comprised between infinity and centimeters (cm), preferably above 4 to 6 meters. A distance of intermediate vision is typically comprised between 65-70 and 40 cm. A distance of near vision is typically below 40 cm, preferably comprised between 40 and 33 cm.

Preferably, the relative positions of the visual test screen 21, the optical element 30 and the exit aperture 10A are adapted to be varied in order for this first distance D1 of projection between the visual test image OPT produced and the exit aperture 10A to be continuously modified inside one or several ranges of optical distances (first distances D1) between infinity and a near vision (NV) distance.

Preferably, the first distance D1 between the visual test image OPT produced and the exit aperture 10A may take any value comprised between infinity and a near vision distance.

The visual test picture displayed by the visual test screen 21 is for example an optotype. Other types of picture adapted to test the vision of the individual may be used, as known by the man skilled in the art. The acuity module 20A is thus designed to produce visual test images (representing an object, such as an optotype) for the individual's eye 1.

The optical element 30 comprises here an optical lens 31. Lens 31 is here an achromatic lens, having an effective focal length between 70 cm and 100 cm (1 meter), preferably of about 80 cm, for instance. It comprises for example an achromatic doublet. It may also be for example a simple lens such as e.g. a plano-convex lens or a more complex lens such as an aspherical lens. In the case where a simple lens is used, this simple lens has preferably an effective focal length of more than 80 cm to limit chromatic aberrations.

The effective focal length (usually referred to as "EFL") of the lens 31 corresponds to the optical power of the lens itself. It is measured between a focal plane of the lens and a theoretical plane placed inside the lens (known usually as "principal image plane"). As it is not easy to position optical elements relative to the lens using the effective focal length, the position of the theoretical plane being difficult to precisely determine, a back focal length may be used.

The back focal length (usually referred to as "BFL") of the lens 31 is measured between the last diopter summit (i.e. vertex) of the lens and the focal plane of the lens along an optical axis L (see FIG. 2) of the lens 31, that is to say from the back surface of the lens to the focal plane of the lens 31.

As explained later, the optical axis L is here folded by the use of reflective surfaces such as mirrors (see FIG. 2).

Alternatively, the use of lenses with a small effective focal length, for example 20 cm, is possible with a smaller screen such as a miniature screen of about 1 inch (=2.54 cm) with high resolution HD, full HD or even 4K/8K. This could be used for obtaining a smaller device.

Preferably, the optical element 30 and the visual test screen 21 are arranged relative to each other so that there is at least one relative position of the optical lens 31 and the screen 21 for which the screen 21 is placed at a distance from the optical lens 31 equal to the back focal length of said lens 31.

Therefore, in a far vision configuration, while the lens 31 is placed on the visual test optical path of the light, the relative position of said screen 21 and said lens 31 may be adjusted for the screen 21 to be located at a back focal length from said lens 31.

This way, the visual test image generated by the display module 20 may be placed at infinity relative to the exit aperture 10A, and therefore, the eyes of the individual. The distance between the visual test image produced and the exit aperture is then set as infinite.

As shown in FIGS. 2 and 3, the optical element 30 is movable between:

- the first active position where the optical path of the light beam emitted by the screen 21 and travelling to the eye 1 of the individual goes through the optical element 30, and
- the second retracted position where the optical path of this light beam avoids the optical element 30.

In the case of the optical element 30 being a lens 31, the light beam goes through the lens 31 when it is in the active position and does not go through the optical lens 31 when it is in the retracted position.

Thanks to this, the visual test projection sub-system 20A (acuity module) is adapted to produce the image of the visual test picture at a variable distance for the individual's eye 1.

In practice, here, the optical element 30 comprises the lens 31. It is fixed on a support 32 that is pivotally mounted on part of the casing 2 of the optometry device 100.

In a first angular position of the support 32 of the lens 31, shown for example on FIG. 2, the support 32 is parallel to the visual test optical path of the light and brings the lens 31 across this optical path: the light emitted by the first screen 21 then goes through the lens 31. The visual test optical path of the light follows at least partially the optical axis L of the lens 31.

In a second angular position of the support 32 of the lens 31, shown for example on FIG. 3, the support 32 is inclined/pivoted relative to the visual test optical path of the light and brings the lens 31 outside this optical path: the light beam emitted by the first screen 21 then avoids going through the lens 31.

Of course, the geometry of the support 32 allows it to remain out of the optical path at all angular position of this support 32.

The support 32 is pivotally mounted in order to be able to pivot about a rotation axis X1 perpendicular to the optical path of the light beam at the position of the lens 31 when it is place in the first angular position. In other words, the rotation axis of the lens 31 is perpendicular to the optical axis L of the lens 31.

In the example described here, the lens 31 is of rectangular shape. It is inserted inside a frame that surrounds its edge. Two triangular branches link the frame to the pivot axis of the lens 31. A rectangular ring keeps the lens 31 in place in the frame. This ring is mounted thanks to screws on the sides of the frame facing the pivot axis.

Preferably, the visual test screen 21 is movable in translation along two perpendicular directions for centering this screen 21 relative to the other optical component of the optometry device 100, in particular relative to the optical axis L of the lens 31 in its active position.

Motorized active recentering of the first screen 21 may be implemented. Alternatively, the screen may be centered for predetermined fixed positions only.

Thanks to the adjustment devices, the screen 21 is accurately centered relative to the optical center of the lens 31. This centering step ensures that the light emitted at the center of the screen exits the optometry device at the center of the exit aperture 10A.

The size of the mirrors and lens is chosen to be wide enough to enable easy centering of the visual test image. The minimal distances between screen, mirrors and lens may also be enlarged to facilitate this centering.

Moreover, in addition to this physical centering of the screen, a numerical centering correction may be applied to the visual test picture displayed by the screen 21 in order to compensate predetermined deviation of the screen or other optical component, in particular the reflecting surfaces in predetermined configurations of the device. This numerical centering correction consists in shifting the visual test picture on the screen in order for it to appear centered relative to the exit aperture. The control unit 28 may be programmed to implement this correction of the visual test picture.

The physical and numerical centering adjustments aim at maintaining said visual test image visible for the eye 1 of the individual through the exit aperture 10A of the optometry device 100 centered for all relative positions of the optical components of the device.

Thanks to the adjustment devices, the visual test picture displayed by the visual test screen 21 may be accurately centered relative to the optical axis L of the lens 31.

When the first screen 21 and/or the visual test picture displayed by the screen 21 is accurately centered on the optical axis L of the lens 31, the screen axis considered at the center of the picture displayed, the optical axis L of the lens 31 and the optical path of the light coincide inside the display unit 20.

Between the display unit 20 and the refraction test unit 10, the optical path of the light may deviate from the optical axis L of the lens 31, as the refraction test unit 10 and thus the exit aperture 10A are placed on front of the eye 1 of the individual and may therefore be shifted relative to the optical axis L of the lens 31.

In the embodiment described here in more details, the acuity module 20A of the display unit 20 also comprises at least one reflecting surface 41. This reflecting surface 41 is arranged in the optometry device 100 in order to direct the optical path toward the exit aperture 10A of the refraction test unit.

The reflecting surface 41 allows folding the optical paths of the light beams emitted by the screens 21, 22, in order to limit the size of the display module 10.

In practice, the at least one reflecting surface comprises at least one mirror 41, preferably between two and four mirrors.

Alternatively, said reflecting surface may comprise any kind of beam splitter. Or, alternatively, in a simplified embodiment, the optometry device may comprise no reflecting surface at all. In this kind of embodiments, the first screen is then placed on the optical axis of the lens or of the optical element, and preferably movable in translation along the optical axis of the optical element. The optical axis of the lens is then straight, as it is not folded by the mirrors.

Moreover, the at least one reflecting surface may be movable in translation and/or in rotation between at least two positions.

The reflecting surface may be movable in order to further vary the distance between the visual test image and the exit aperture.

The second projection sub-system or "scene module" 20B comprises here the second or scene screen 22 and an additional mirror 24. The additional screen 22 is used to display the background picture. This background picture is preferably of an environment familiar to the individual, for example a natural environment, exterior or interior, such as a city, a landscape or a room.

The additional mirror 24 is here a concave mirror. Its optical axis goes through the summit of the concave mirror 24 and is here overlapped with the optical axis L of the lens 31 of the acuity module 20A at the exit from the display unit 10.

The additional screen 22 may be a video display, for instance an LCD display, or any adapted screen of the type described earlier in reference with the visual test screen 21 of the acuity module 20A.

A beam splitter 26 is placed between the acuity module 20A and the scene module 20B in order to superimpose the light emitted by the screen 21 of the acuity module 20A (visual test optical path) and the light emitted by the second screen 22 of the scene module 20B (background optical path).

Advantageously, the beam splitter 26 is positioned such that it reflects the light coming from the first screen 21 of the acuity module 20A towards the refraction test unit 10 and, ultimately, towards the eye 1 of the individual. It also reflects the light emitted by the second screen 22 towards the additional mirror 24 and let the light reflected by the latter travel straight through it towards the eye 1 of the individual. Both light beams, coming from the acuity and scene modules 201A, 20B exit the casing 2 of the display module 10 through an opening 3.

As represented in FIGS. 2 and 3, the visual test screen 21 of the acuity module 20A and the second and third mirrors 42, 43 are here fixed and not mobile.

In alternative embodiments, first screen and the second and third mirrors may be mobile in translation and/or rotation.

The first mirror 41 is here placed on the visual test optical path and mounted to pivot about a rotation axis X1 perpendicular to the optical path of the light beam, in order to be alternatively placed at an angle of 45° or 135° relative to the screen axis S of the visual test screen 21.

Hence, the light emitted by the screen 21 can here follow one of three optical paths (all are "visual test optical paths"), depending on the angular position of the first mirror 41.

When the first mirror 41 is in the first position (45° to the screen axis S), and the optical element 30 is in its active position (FIG. 2), the light (emitted by the first screen 21) is reflected by the first mirror 41, towards the second mirror 42, and by the second mirror 42 towards the third mirror 43, and by the third mirror 43 towards the optical element 30 and the beam splitter 26.

The distance between the visual test image produced by the projection optical system 20A, 20B and the exit aperture 10A is then about 6 meters: the visual test picture displayed by the visual test screen 21 is then seen at a distance of about 6 meters (more or less equivalent to "infinity") by the eye 1 of the individual. With no other modification, the optical element 30 may be pivoted to its retracted position. The distance between the visual test image OPT and the exit aperture 10A is then about one meter.

The first mirror 41 may then be pivoted from its first position (FIG. 2) to its second position (135° to the screen axis S, see FIG. 3). The light beam emitted by the first screen 21 is then reflected by the first mirror 41 directly towards the beam splitter 26 of the display unit 20 and then reflected by the beam splitter 26 towards the eye 1 of the individual. The distance between the visual test image and the exit aperture 10A is then about 40 centimeters (in the configuration of FIG. 8).

The visual test image may therefore be displayed at three fixed distances from the exit aperture of the device.

With this optometry device 100, the visual test image OPT (the one containing the figures to test the acuity of the eye) may be observed at three (or even more) different optical distances by the individual.

It should be noticed that that the actual sizes (height×width H×W in $cm^2$) or apparent sizes (angular height×width in degrees) of the visual test images OPT at different distances D1 are usually different due to the fact that the overall dimensions of the first screen 21 are constant whereas the visual test distances D1 or projection are variable.

Figure 4:
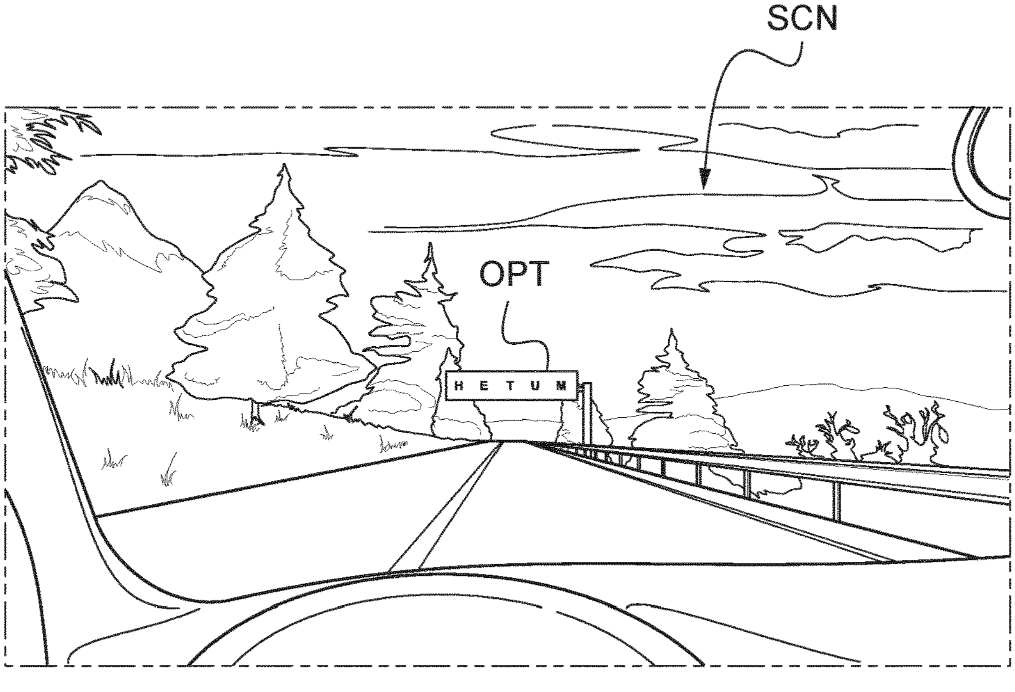
FIG. 4 shows an example of a visual test image in superimposition with a scene image.

As already explained, FIG. 4 shows an example of a visual test image OPT projected (along the visual test optical path) by the display unit 20 to the eye 1 of the individual in superimposition (along the background optical path) with a scene image SCN.

Here, as shown in FIG. 4, the scene image SCN or "scene" represents different elements appearing in a relatively bright background (i.e. of high luminance: for example superior to 100 $cd/m^2$, preferably to 200 $cd/m^2$, more preferably to 200 $cd/m^2$, and even more preferably to 300 $cd/m^2$), and arranged as a natural and/or realistic scene for the individual, such as a road in a landscape (trees, hills, clouds, etc. . . . ) seen through the windshield of an automobile (we see a part of the dashboard, steering wheel and of the rear-view mirror of the automobile). In this given example of FIG. 4, the corresponding scene picture, as set on the scene screen by the control unit, depicts these elements and background.

The visual test image OPT or "optotype" (as it is designed to test the acuity) is represented in the form of a road sign placed far away above the road on which the car is running. The visual test image OPT shows here a sequence of capital letters, from left to right: 'H', 'E', 'T', and V'. In the case of FIG. 4, those letters are projected and seen by the driver (i.e. the eyes 1 of the individual) at a far distance of vision, here at a distance of around 15 meters (equivalent to infinity for the eyes). The letters of the optotype OPT have thus the adequate angular sizes to test the acuity of the individual for far distances. In this given example, the corresponding visual test picture (not shown) includes the same sequence of optotypes and a background (of the rectangle form) on which the optotypes are disposed, said background being of high luminance (for example superior to 150 $cd/m^2$, preferably to 200 $cd/m^2$, more preferably to 300 $cd/m^2$), and said optotype of low luminance inferior to 100 $cd/m^2$, preferably to 50 $cd/m^2$, more preferably to 30 $cd/m^2$.

On this FIG. 4, the visual test distance D1 of the visual test image OPT is set at far distance, and so the scene distance D2 of the scene image SCN. Due to the projection of the visual test picture by the projection optical system 20A, 20B at the visual test distance D1, the visual test image OPT appears to the individual with smaller dimensions than the scene image (ratio between 1:10 and 1:100 for example). In this configuration, the visual test image is superimposed with the scene image on a superimposition area at the center of the scene image and appears surrounded with the elements and background of the scene image disposed outside the superimposition area.

For other visual test distances D1, for example smaller than far distance, the visual test image appears to the individual greater in size and occupies a bigger space on the scene image, with the same shape and aspect ratio of the visual test image OPT observed at far distance. The superimposition area between the two images is also bigger in size.

Whatever the visual test distance D1 is, if nothing is done on the different pictures displayed on the screens 21, 22 of the display unit 20, the visual test image OPT would be projected on a bright region of the scene image SCN of the superimposition area, and would have its contrast disturbed by the luminance of the scene image in this superimposition area.

Moreover, for other visual test distances D1 (there could be more than 5 meters differences between near and far visual test image distances), the visual test image appears to the individual with a different (bigger in the present example) size though with the same shape and aspect ratio so that it may influence badly how the optotypes OPT (letters) are seen by the driver.

That is the reason why the present invention is interesting. Indeed, according to the invention, in the optometry device 100 described above, the at least one control unit 28, 29 is configured to define in the scene picture at least one scene zone implying transparency for the corresponding virtual scene image and in the superimposition area between the visual test image and the scene image, allowing the individual's eye to observe the functional zone of the virtual visual test image OPT without contrast decrease, at the visual test distance D1.

Moreover, the control unit is configured to modify the luminance or colorimetry distribution of the visual test image OPT and/or of the scene image SCN based on the visual test distance (first distance D1) of projection of the visual test image OPT.

Therefore, it is possible to change the way the different projected images are seen by the individual.

In some embodiments, the at least one control unit may also be configured to perform the luminance/colorimetry modification as a function of the visual test distance (first distance D1) of projection.

In some embodiments, the at least one control unit drives the projection optical system to produce a visual test picture whose luminance depends on the main color temperature, preferably according to the Kruithof's curve. For example, for a color temperature of 5000° K, the luminance of the scene screen will be set at 120 cd/$m^2$ and for 5500° K, the luminance of the acuity screen will be set at 160 cd/$m^2$ for defining a bright background, and to 85 cd/$m^2$ for defining a dark background.

In possible embodiments where the optometry device comprises only one control unit, this unique control unit is configured to control both the first and second projection sub-systems 20A, 20B, and more particularly the first and second screens 21, 22.

In other embodiments, like the one represented in FIGS. 1-3, where the optometry device comprises two control sub-units 28, 29, each control sub-unit 28, 29 is configured to control its associated screen 21, 22 respectively.

Because the optical image of the "acuity" channel is a virtual image for the individual, the scene image SCN of the "scene" channel projected by the second projection sub-system 20B appears in transparence through the acuity channel in such a way that the visual test image, i.e. the optotypes OPT, is seen by the individual with a low or lower contrast, rendering its recognition more difficult or longer.

Hence, in order to overcome that particular problem, the second control sub-unit 29 of the scene module 20B drives the scene screen 22 to apply a zone implying transparency on the scene image SCN, the zone implying transparency having a shape and an aspect ratio substantially identical to a shape and aspect ratio of the visual test image SCN.

Figure 5:
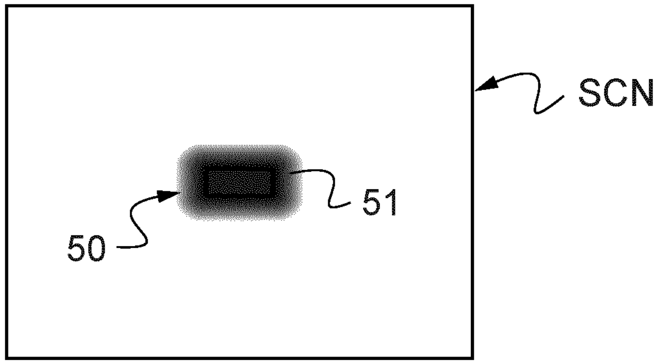
FIGS. 5 and 6 show examples of zone implying transparency that can be applied to the scene picture creating the scene image displayed by the optometry device of FIG. 1.
Figure 6:
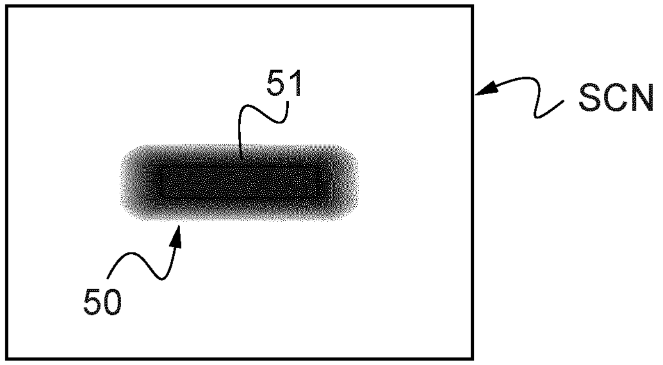

In other words, and as shown in FIGS. 5-6, the second sub-unit 29 creates a zone implying transparency 50 in the scene picture displayed on the second screen 22. This zone implying transparency 50 is projected on the scene channel, has usually a rectangular shape and an aspect ratio in accordance with the visual test image OPT projected on top of it.

In practice, the zone implying transparency 50 is created by driving the corresponding pixels of the scene screen 22, and more precisely by decreasing/suppressing their luminance level. For example, the colorimetry distribution of the zone implying transparency is configured by the control unit to have a low luminance inferior to 100 cd/$m^2$, preferably to 50 cd/$m^2$, more preferably to 30 cd/$m^2$.

Preferably, the zone implying transparency 50 presents a size (height×width in the scene image) which is larger than a size of the visual test image OPT (here the size of the road sign in FIG. 4), for example 5 to 33% larger, even more preferably between 10 to 20% larger.

This larger size allows taking into account the fact that the inter-pupillary distance of the subject (i.e. the physical distance between the two centers of the pupils of the eyes 1 of the individual) induces a parallax effect when the visual test image is observed with left and right eye.

The oversize of the patch 50 depends of course upon the visual test distance D1 of projection of the visual test image OPT.

Advantageously, the projection control unit 29 drives here the scene screen 22, to produce a scene picture so that a peripheral zone 51 of the scene image SCN is fuzzy, as represented on FIGS. 5 and 6.

By doing this, it is possible to use the same zone implying transparency whatever the inter-pupillary distance of the subject is.

This fuzzy contour of the scene image SCN is obtained directly by letting the corresponding pixels of the second screen 22 display a background picture with fuzzy regions.

Preferably, the zone implying transparency has a relative position in the scene image SCN (i.e. the scene in which the visual image is included) which depends on the tested individual's eye 1 (left, right, or left and right eyes for binocular tests) and also on the visual test distance D1 of projection.

In this way, it is possible to overcome parallax effects during the visual tests. For, the zone implying transparency 50 in the scene image SCN is positioned so that it is superimposed in the region of the optotypes OPT, thus decreasing the background luminance in this region and then increasing the visually perceived contrast of the optotypes by the eye 1 (or eyes) of the subject.

Examples (Zone Implying Transparency in the Scene Image)

For a far vision (FV) visual test, as represented on FIG. 5, we create through the background channel (i.e. along the background optical path) a black (or any other dark color) rectangle 50 (or any other shape fitting with the visual test image observed at the visual test distance D1) preferably with fuzzy edges 51 that constitutes in the scene picture, the zone 50 that will imply for the scene image transparency. This zone implying transparency 50 is centered in the background picture for binocular vision testing.

When we mask one eye of the subject to test the monocular vision, a parallax effect occurs. The parallax is an effect due to the change of incidence of the line of sight of the patient, that is a change of position of the observer while observing an object (e.g. the optotypes OPT on the road sign of FIG. 4).

For example, when we test the right eye 1, the black rectangle 50 should be shifted to the left and in the opposite direction if the left eye is under test.

Here, the black rectangle 50 has a width (W) of 127 mm and an height (H) so that the aspect ratio W/H of width/height is the same as Full HD, that is W/H=1920/1080 (≈1.78).

Moreover, we "add" a 20% blur to the rectangle 50 then creating the blurry contour (or fuzzy edges) shown in FIG. 5. It's like applying an "out-of-focus" effect to the background picture displayed on the second screen 22. Then, the width of the rectangle 50 becomes 175 mm. This zone implying transparency 50 is centered for binocular vision or shifted by 3 mm to the right (or to the left) for the visual testing of the left eye 1 (or for the right eye respectively).

The fuzzy edges imply a larger size of the zone implying transparency 50, for example of 10, 20 or preferably 25% larger in size. The perception of transparency and the width of the fuzzy edges can be chosen according to the specific scene image and to the specific acuity image. The skilled man can chose the best transparency/width of the fuzzy edges further to different trials made with the same specific scene image and to the specific acuity image and different transparency/width of the fuzzy edges. The transparency/width of the fuzzy edges implying the best esthetical perception of the integration of the acuity image to the scene image will be selected for this specific scene image and the specific visual test (acuity) image.

For a monocular near vision (NV) visual test, we can use the same rectangle as the one of FIG. 5 used for far vision (FV). Yet, it is shifted to the right or to the left from 67 mm, due to the parallax effect mentioned above. This parallax effect is much stronger at near distances than at far distances.

For a binocular near vision (NV) visual test, we must use a large or larger patch such as the black rectangle 50 represented in FIG. 6.

In this figure, the zone implying transparency is used for a 40 cm visual test, thus in near vision, for both eyes (binocular). The rectangle 50 has a width (W) of 253 mm, again with a full HD aspect ratio of 1920/1080 and a 20% blur on the edges 51 of the rectangle. The width of the zone implying transparency 50 then becomes 363 mm and is centered on the scene channel.

That widening of the zone implying transparency is needed due to the fact that the projection of the visual test screen, that is the visual test image OPT, in the scene channel is wider for near vision/small distances (test image at 40 cm and scene image at infinity) than for far vision/large distances (test image at 6 m and scene image at infinity).

Displaying a larger black rectangle in that case allows:

minimizing the physiological diplopia of background scene in near vision (here the scene channel on which the patch is applied); and masking/hiding the "white" or brighter area formed in the superimposition area at the center by transparency through the test image of the test channel (which corresponds here to the splitting of the zones implying transparency with the white background between the two), which would disturb the patient and the reliability of the eye exam.

Examples (Zone Implying Transparency in the Visual Test Image)

Because the size of the visual test screen 1 is fixed (constant) and because the optical formation of the visual test images OPT through the acuity channel (visual test optical path) is done with different image magnification for different visual test distances D1 of projection, the apparent size of the visual test images OPT varies greatly between far, intermediate or near vision.

Indeed, when we perform a visual test at a nearer distance (i.e. first distance D1), then the visual test image OPT appears globally bigger than at farther distances.

Therefore, in order to keep the same apparent size L×l of the test image i.e. the functional part including the optotypes and their background, the visual test control unit 28 drives the projection sub-system 20A to produce the visual test images OPT from a visual test picture with a frame implying transparency 52 surrounding the functional zone L×l of the visual test picture. The frame 52 shape features are modified based on said visual test distance D1 so as the functional zone of the visual test image OPT has a shape and an aspect ratio L×l substantially identical for different visual test distances D1.

Indeed, when we apply a dark/black region like a frame on the visual test picture produced by the screen 21, it appears for an observer, i.e. for the eye 1 of the patient, as being transparent in the visual test image, thus allowing the vision of the scene image SCN (scene channel) corresponding portion through it.

Figure 7:
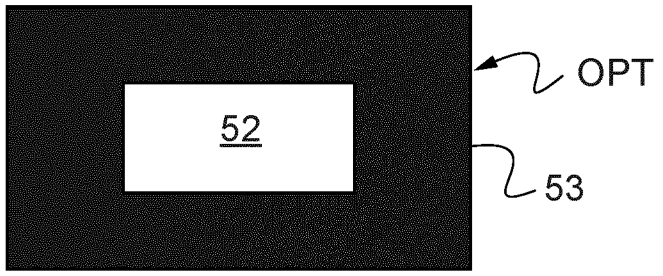
FIGS. 7 and 8 show examples of a frame implying transparency that can be applied to the visual test picture creating the visual test image displayed by the optometry device of FIG. 1.
Figure 8:
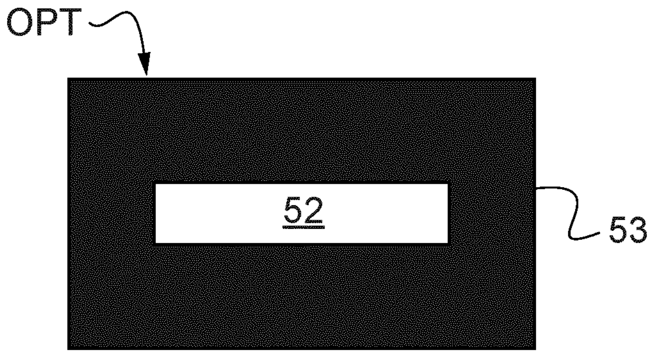

The FIGS. 7 and 8 illustrate this embodiment of the optometry device 100. By adding the black frame 53 on the visual test optical path, with dimensions chosen so that the functional parts 52 of the different visual test images produced at the different visual test distances D1 are substantially identical, then the functional zone (optotypes) of the visual test image OPT has the same shape, aspect ratio and apparent size for different visual test distances D1 of projection.

This frame 53 can be set by the control unit to have a low luminance inferior to 100 cd/m$^2$, preferably to 50 cd/m$^2$, more preferably to 30 cd/m$^2$, by setting the corresponding pixels of the visual test or acuity screen producing the visual test picture.

Advantageously, the black frame has a rectangular shape and the same aspect ratio as the first screen 21. The exterior of the black frame 53 has the same size as the acuity screen 21. Then, the "thickness" of the black frame 53 is adjusted by the projection optical system as a function of the visual test distance D1 of projection.

More precisely, in order to obtain the same apparent size L×l of the visual test image OPT at any visual test distance D1 of projection, we create a black frame on the visual test picture displayed by the screen 21 of the acuity module 20A.

It can be done easily, for example by darkening (i.e. decreasing the luminance) or even switching off the corresponding pixels of the first screen 21.

In FIG. 7, the black frame 53 has an exterior width (total width) of 1920 pixels with a full HD aspect ratio (around 1.78). In its interior dimension, the black frame 53 has dimensions equal to 254×120 mm$^2$.

Here, the variation of the image magnification of the second optical sub-system 30 is 0.533 (the NV test image is thus around 1.88 times bigger than the FV test image), the visual test image OPT will thus appear with the same overall size in near vision and in far vision conditions.

Examples (Positioning Frame for Bright Optotypes in a Dark Background)

For specific visual test image implying bright optotypes in a dark background, in addition to the above possibilities considered alone or in combination, a positioning frame can be produced in the visual test picture to make said bright optotypes in a dark background, perceived by the individual as being positioned at a particular depth of observation.

Indeed, without such a frame, said bright optotypes shown in a dark background are observed by the individual in an also dark scene image, the bright optotypes would appear as floating in the image, what can disturb the individual.

The positioning frame acts is perceived a support for the optotypes what can be conceived by the individual brought to handle the refraction test without disturbance.

For this purpose, the control unit 28, 29 is configured to define:

- the functional zone 52 of the visual test picture with a low luminance inferior to 100 cd/m$^2$, preferably to 50 cd/m$^2$, more preferably to 30 cd/m$^2$, to produce a dark or low luminance background on the visual test image;
- optotypes with a high luminance superior to 200 cd/m$^2$, preferably to 250 cd/m$^2$, more preferably to 300 cd/m$^2$, to produce for the corresponding picture, bright optotypes positioned in a low luminance background; and
- in addition a positioning frame 54 surrounding the functional zone 52 and of a higher luminance than the functional zone 52, superior to 200 cd/m$^2$, preferably to 250 cd/m$^2$, more preferably to 300 cd/m$^2$ in order to define for the corresponding picture a bright positioning frame for the bright optotypes positioned in a dark background. The positioning frame can be constituted by a white frame 54 surrounding a rectangle dark background and bright optotypes of the functional zone of the visual test image.

Of course, preferably, an adapted frame implying transparency in the visual test image 53 as disclosed above can also be defined around the positioning frame 54 so as to ensure the functional zone 52 surrounded by the positioning frame to show substantially identical size, shape and aspect ratio for different visual test distances D1.

Preferably, the positioning frame will be defined with a realistic shape according to the pending visual test distances D1. Accordingly, for short visual test distances D1 to determine refraction at near distance, the positioning frame can take the form of an object usually looked at near distance and defining a frame, such as a smartphone. The positioning frame will be defined so as to match the shape/aspect ratio and apparent size of the surrounding edge of said smartphone looked at the chosen visual test distance. On the contrary for long visual test distance to determine refraction at far distance, the positioning frame can take the form of an object usually looked at far distance and defining a frame, such as a road sign. The positioning frame will be defined so as to match the shape/aspect ratio and apparent size of the surrounding edge of said smartphone looked at the chosen visual test distance.

Now, we will discuss how the colorimetry changes are handled in the optometry device of the invention.

Because the different optical paths in the optometry device 100 are different and also vary between a near vision test and a far vision test (at least for the visual test optical path), then the luminance and the colorimetry (e.g. color temperature) of the visual test image OPT (acuity channel) can also change for the patient doing a refraction test at different distances.

Therefore, in preferred embodiments, the first control unit 28 of the optometry device 100 drives the projection optical system 20A (acuity module) to produce a greyscale visual test image having a white color temperature and an overall luminosity which are constant with varying visual test distances D1 of projection.

Like this, it is possible to keep the same lighting/color conditions of the visual tests at variable image distances.

In practice, we adjust two parameters:

- the (white) color temperature (in Kelvins) of the white point along the visual test optical path; and
- the luminance level (i.e. brightness in candela/m$^2$) of the visual test image.

These two parameters are directly adjusted in the visual test picture displayed by the first screen 21.

Moreover, in order to bring even more comfort to the patient, the brightness and color temperature of the scene screen 22 is different from those of the acuity screen 21.

All those techniques are really easy to implement and they allow performing visual tests in a compact system and in a comfortable manner for the patient.

In an example embodiment of the optometry device 100, it has been determined, on one hand, that the output luminance of the scene image SCN (measured with a spectrophotometer) should be, at any distance, equal or higher than 350 cd/m$^2$. On the other hand, the output luminance of the screen 21 in the acuity channel should be above 375 cd/m$^2$ at any test distance.

To obtain these values, it is possible to adjust the brightness and/or the white point of each backlight unit of the screens 21, 22 (if they are standard LCD displays).

For example, we determined that the overall color temperature that is needed for the screens 21, 22 is around 5000 K±200 K. To obtain that value, the color distribution of the background picture (scene channel) and of the visual test picture (acuity channel) are adapted and chosen as a function of the visual test distance D1 of projection.

The above mentioned optometry device 100 as illustrated in FIGS. 2 and 3 allows the subject to live an immersive experience as looking into a box, such as with a reality augmented headset, compared to traditional refraction determination method taking place in a whole refraction room involving a screen displaying an image and placed at 4 or 6 meters from a person positioned in front of a phoropter.

The object of another aspect of the invention, is to provide to the subject specific global images i.e. including acuity and scene images whatever their constitution (either deriving from the superimposition of a visual test (acuity) and a scene image as disclosed above, or constituted by a unique image containing both scene zone and acuity zone) during the refraction test specifically created and optimized to render the experience the more realistic while being the more convenient to determine refraction.

Of course the global image according to this embodiment as described below, could also be displayed on the screen of the above mentioned traditional refraction determination method but with less impression of immersion for the subject due to the physical distance with the screen and the external elements surrounding the latter, as disclosed in the FIG. 15.

We revert now to the optical system as disclosed in the FIGS. 2 and 3, which allows to display in an immersive way the visual test (optotype or the like) with a context brought by a surrounding scene in a realistic and comfortable environment for the observer to effectively measure visual functions virtually at several distances.

It is however essential to provide the global image with a minimum of clues of perception that are usually naturally present in real life to reach the perception of immersive experience, otherwise the attempt to provide the more realistic image for the subject would lead to unwanted perception and therefore unwanted response from the visual and cognitive system of the patient and disrupt the proper performance of the visual examination.

Conversely, the inventors have discovered that cautions have to be taken not to reproduce in the global image all of the aspects encountered in natural observation at different distance of observation, to avoid the patient to adopt unwanted position that would deter the examination.

The proposed solution consists therefore in precisely defining the composition of the global image shown during the refraction test, in order to allow the correct performance of the visual examination carried out at several distances in an immersive environment while warrantying a correct posture of the patient.

This object is reached thanks to several elements of the global image acting as clues of distance perception combined with specific choice in the way the optotypes are displayed relatively to the patient.

Figure 9:
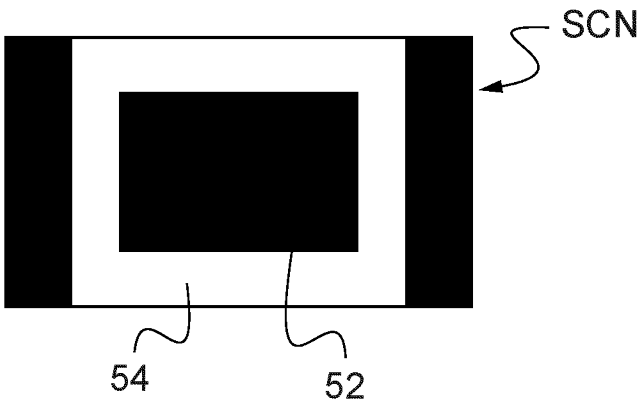
FIG. 9 shows an example of a visual test image of a positioning frame that can be applied to the visual test picture creating the visual test image displayed by the optometry device of FIG. 1.
Figure 10:
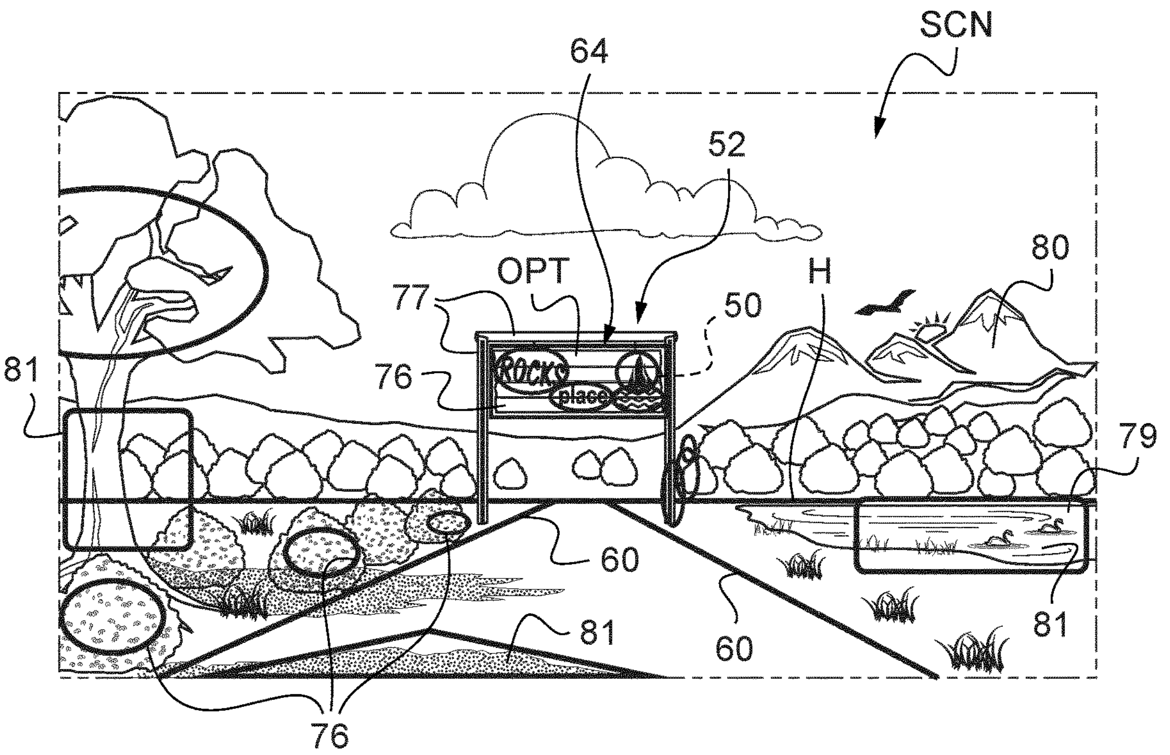
FIGS. 10 to 15 are a set of pictures comprising a visual test picture and a scene picture useful for the optometry device of FIG. 1
Figure 11:
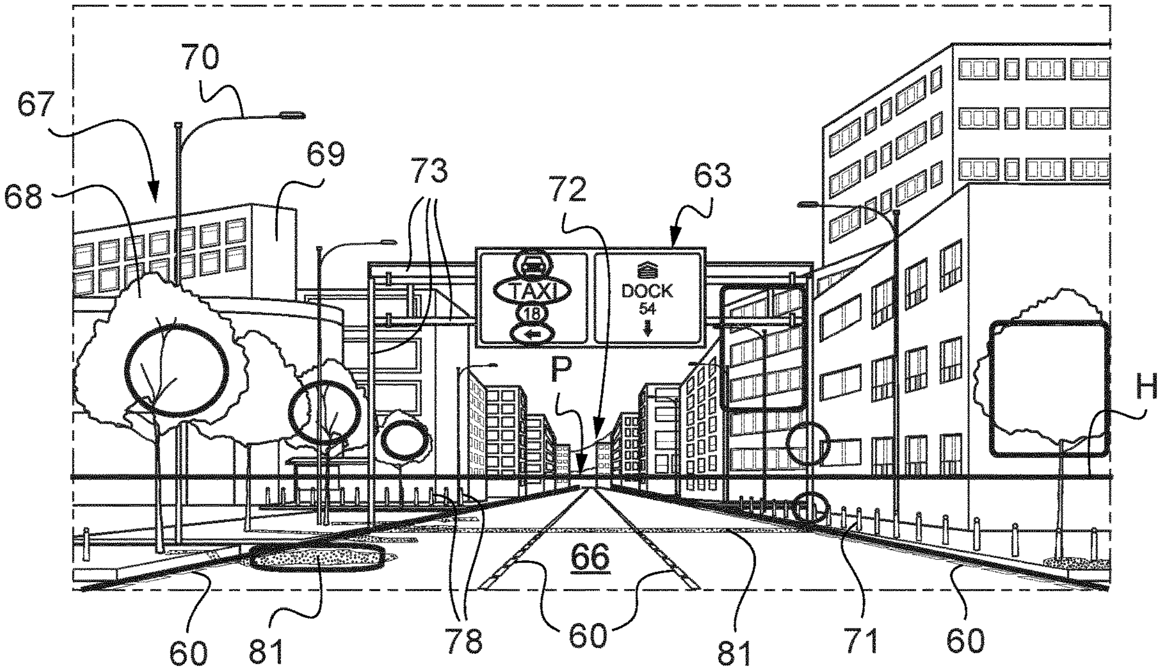

More precisely, the global image according to the invention, as disclosed on the FIGS. 9, 10 and 11 comprises at least two opposed vanishing lines 60 oriented in the direction of the functional acuity zone of the global image wearing the symbols allowing the refraction determination. Moreover, the functional zone is defined such that it appears on the global image shown to the observer looking straight across the phoropter's lenses, as being displayed in a vertical plane for an observer, whatever the visual test distance D1.

And when the global image is composed of the superimposition of an acuity image to a scene image, formed respectively from a scene picture and an acuity (visual test) picture as disclosed above, the vanishing lines 60 are oriented toward the zone implying transparency 50 and the acuity picture takes the form of a panel seen from the front and wearing symbols positioned flat thereon.

Figure 12:
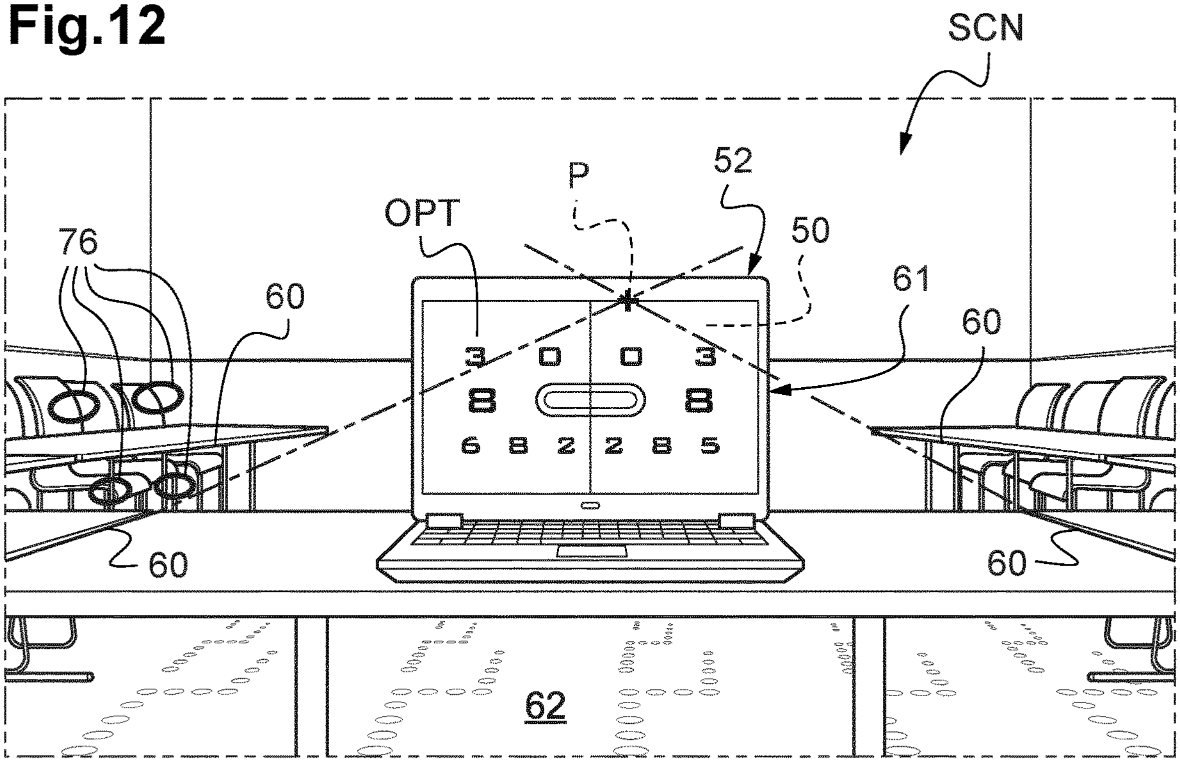
Figure 13:
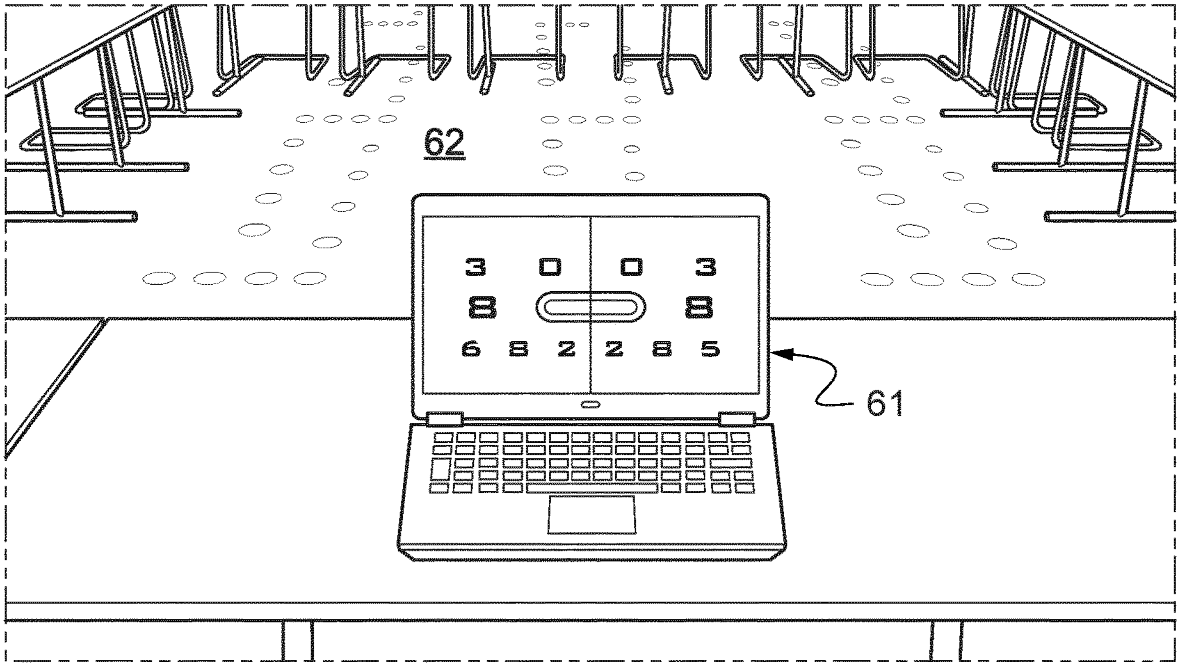
Figure 14:
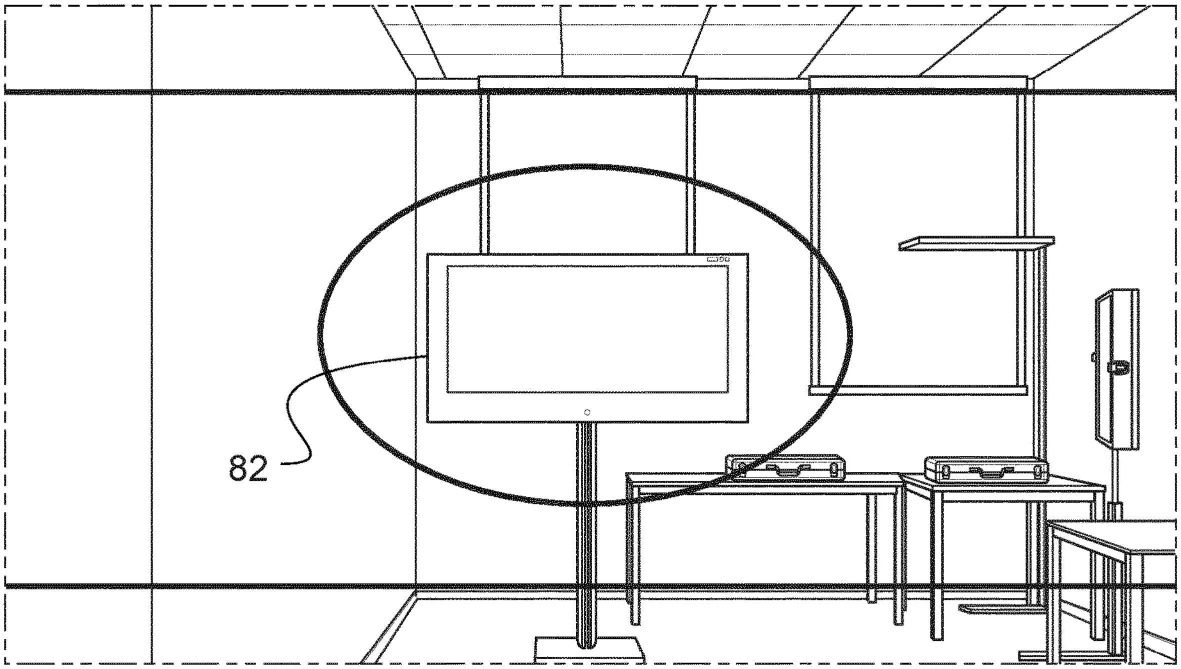

More precisely, the comparison between the FIGS. 11 and 12, allows to better understand this last feature according to the invention illustrated for a near/intermediate testing distance.

To test in the more realistic conditions the near/intermediate vision, the symbols used to determine refraction are disclosed on the image as being integrated in an object used to be observed at the chosen near/intermediate distance by a subject (a laptop 61 in the present example, a smartphone, a book, a menu card for other near/intermediate vision testing . . . ).

Also, the scene surrounding this object 61 disclosing the symbols is chosen to incorporate in the most realistic manner said object observed at the chosen distance.

In the illustrated example, this surrounding scene comprises tables of a meeting room disposed in a C configuration, with two opposite rows of table and corresponding rows of chairs disposed along the vanishing lines, acting as clues of perspective perception, the laptop being disposed in a front row of tables, at the center of the picture. The impression for the subject is to look at the screen, while being sitting on a chair facing said table, knowing that the subject is sitting on a chair during the test, looking straight forward through the phoropter of the optical system). The laptop supported by the table and more specifically its frame and keyboard act as a transitional element between the screen of the laptop displaying the symbol and the environment meeting room.

Vanishing lines 60 are displayed thanks to the rear edges of the lateral tables and thanks to the lateral edges of the central table on which the laptop is disposed, as converging toward points P disposed above or into the functional zone wearing the optotypes (the laptop's screen) and in any case, close to an horizon line. They moreover appear to be symmetric one another.

Even if the angle of view from above of the FIG. 12, would be the more realistic for a subject in view of the scene depicted described above, since the head of the subject facing such situation in the real life would be disposed above the laptop, this angle of view would have the drawbacks to:

give too much importance to the ground 62 (almost half of the picture) and either incite the subject to change its head posture according to the perception the subject has of the tilt of the laptop's screen or to feel particular discomfort/strange perception if trying to keep the recommended "straight head posture" recommended during the refraction examination, whereas the image looked at defines a clear from above angle of view.

Therefore the straight angle of view of the FIG. 11 is the one chosen according to the invention even if this takes away from realistic conditions. As a result, the ground 62 only occupies only a thin strip at the bottom of the image and there is no gap between the actual posture of the subject (who constantly maintains a straight gaze) and the virtual angle of observation of the object wearing the symbols to determine refraction.

Therefore, for any testing distance, the object wearing the symbols to determine refraction are placed in a plane perpendicular to the straight portion of the light beam 23 exiting the optical system's aperture 10A therefore also perpendicular to the ground.

In the scene depicted, it is moreover important to disclose the symbols used to determine refraction, on an object that fits into the environment. This object must be centered, have a controlled size and be at a coherent virtual distance from the observer (about 6 m in our example for far vision testing and about 40 cm for near vision testing, and between 40 cm and 6 m for intermediate vision testing). The object must be able to be found usually in this context, there must be a link (transition element) between the scene and the support of the object so that it is well integrated and that it is realistic. In addition, the support of the object and the object itself must be universal and present a size that will allow to integrate visual tests while being specific to the condition: e.g. in far vision the object can be a 5° panel, while in near vision the object can be larger (e.g. the contours of a smartphone: 10°). For example, a wooden sign on a country road. For different testing distance, a frame implying transparency can be used in the acuity images, with specific dimensions to render the functional zones of said acuity images for different testing distance, identical in shape and dimensions.

For example, as illustrated on the FIGS. 9 and 10, to test in the more realistic conditions the far vision, the symbols used to determine refraction are disclosed on the image as being integrated in an object used to be observed at the chosen far distance by a subject (a urban road sign 63 for the FIG. 9, or a country road sign 64 for the FIG. 10, a banner floating in the sky, pulled by an airplane in other not illustrated example . . . ). Also, the scene surrounding this object 63, 64 disclosing the symbols, is chosen to incorporate in the most realistic manner said object observed at the chosen distance.

In the illustrated example of the FIG. 9, this surrounding scene comprises a view of a highway defining four opposed and symmetric vanishing lines 60 converging toward a point disposed below the urban road sign, surrounded by peripheral elements 67 composed of repetitive trees 68, buildings 69, street lights 70, street posts 71, disposed along the vanishing line with a size decreasing toward the converging point P and acting as clues of perspective perception for the observer, mountains 72 on the background. The urban road sign 63 is centered on the image, and appears as being supported by a metallic structure 73 fixed on the ground, acting as a transitional element between the urban road sign and the urban landscape. Elements of different natures appearing superimposed acts as additional clues of perspective perception 76 such as the tree 66, street post 70 and building 69 on the left side of the image shown on the FIG. 10.

With this scene, the observer is experiencing a realistic experience, i.e. the same kind of situation as when driving a car sitting on the car seat and looking at the urban road sign, thanks to the perspective perception brought by the vanishing lines, and several repeated/superimposed elements.

However, for the reasons explained above, knowing that the subject is sitting on a chair during the test looking straight forward through the phoropter of the optical system, the angle of view chosen for the subject observing the urban road sign, is not an arising angle of view, as would be in a real situation, but is a straight angle of view and the road sign is instead illustrated seen from the front, with no tilt angle and so are the symbols disposed thereon.

The FIG. 9 depicts the same kind of situation, encountered however in a country landscape. For this purpose, the country road sign is depicted with a wooden texture 76 and the transition element 77 takes also the form of wooden posts 77. The elements acting as clues of perception 76 are here defined by bushes distributed along the vanishing lines 60 defined by the lateral edges of the country road and also along a line H defining the horizon line (whereas in the FIG. 10 of the urban landscape, this line is suggested by the converging point P and posts distributed horizontally 78), by lake and swans 79 dabbling below the horizon line H, and mountains 80 in the background.

Concerning the type of element to be used in an environment, when using a still (fixed) image, it is best to limit the presence of elements that are usually moving in a real environment. Indeed, if we integrate usually moving elements (birds in the sky, persons dancing, jumping, walking . . . ) in a fixed image, this would automatically disrupt the subject's attention, but the presence of living elements displayed in static could give a feeling of oddity. We will therefore endeavor to limit the addition of people and animals in a moving situation, and naturally moving elements (river, waterfall).

Moreover, shadows and reflections 81 smartly spread respectively around or in some of the different elements can act also as clues of perspective perception (thus the shadows of the trees, street light, metallic structure of the FIGS. 9 and 10 and the not illustrated shadow of the chairs on the ground for the near/intermediate vision image of the FIG. 11 . . . the reflection on the surface of the lake . . .).

It was noted that the quality of the image definition and its rendering are particularly important to participate in the realism of the stimulus. Thus, there must be consistency in lighting: depending on the position of the subject, the sun and the shadows. In general, it is necessary for the situation to be known in terms of a bright and relaxing atmosphere while providing a certain unity. The colors can be soft and not garish, united but realistic (sky with large white clouds bringing texture.) In order not to disturb the subject's attention, it is important not to add bright colors at the periphery, or light sources (e.g. reflections on water, . . . ) which may cause any discomfort to the light. It is also important to propose textures to have a realistic and comfortable scene without too repetitive patterns, that are realistic and not disturbing for the subject.

In addition, different levels of blur defined for areas of the scene picture disposed along the vanishing lines, can also act as clues of perspective perception. As such the background areas (mountains 80 on the country FIG. 9, big screen in the meeting room of FIG. 11, converging area P for the urban FIG. 10 . . . ) supposed to be perceived as the farthest from the subject's view point, will have a maximal blur level.

For the other areas than the background area, the level of blur progression will depend on the testing distance D1:

- for far vision testing distance, the far scene will comprise more blurry level for the areas closest to the subject (at the beginning of the vanishing lines), and less blurry areas for the areas closest to the object (at the end of the vanishing line and close to the object showing the symbols or to the zone implying transparency);
- for near vision testing distance, the near scene will comprise more blurry level for the areas farthest from the subject (at the end of the vanishing line), and less blurry level for the areas closest to the subject (at the end of the vanishing line and close to the object showing the symbols or to the zone implying transparency).

A particular advantage of the invention is to also make the symbols used in the test fit to the context of the surrounding scene. As such, the symbols appearing to be displayed on the laptop 61 of the meeting room FIG. 11 are numbers or letters, the symbols appearing on the urban road sign comprise a pictogram representing a taxi, arrays, number surrounded by a circle simulating an indication of a coming exit of the highway in the urban FIG. 10, and pictograms illustrating boat activity and letters written in a relaxed character front a place of leisure for the country FIG. 9.

These symbols appearing on the same object can moreover be different in shape, size, in contrast level, in spatial frequency, in texture, in orientation, in kind among letters, symbols, numbers, pictograms, and/or in relative contrast among reverse contrast (bright symbol on dark wooden background as for FIG. 9) and standard contrast (dark symbol on bright background as for FIG. 10).

Indeed, the test integrated into the object situated in the scene should make it possible to discriminate various visual defects. For this, the test integrated into the object must include several types of stimuli and must have several degrees of difficulty of recognition. The symbols presented must be varied. In addition, they must be universal. For example, a test can be made up of a combination of letters, numbers, and pictograms. It can have different sizes of elements (3/10th to 10/10th), different spatial frequencies, and different textures (wooden planks). It can also include high and low contrasts or reverse contrasts (black on white & white on black) as well as different orientations. Finally, it must include current and short stimuli (Ex: word Taxi, pictogram of a car, . . . ) and not just letters of the alphabet.

Figure 15:
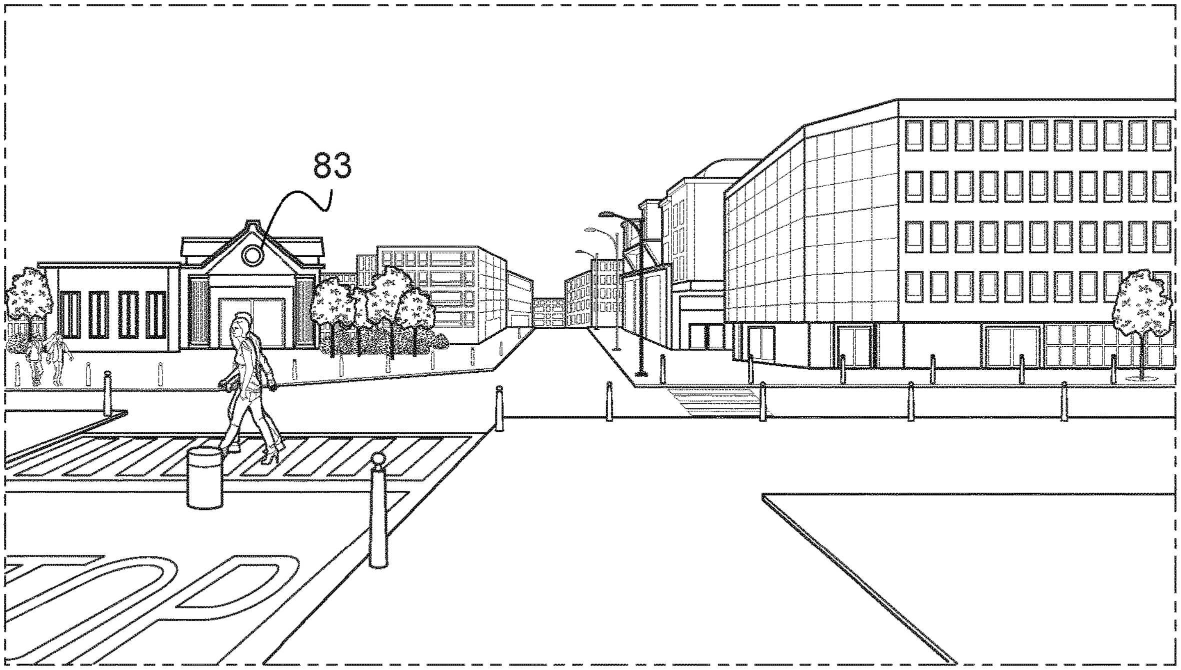

The FIG. 15 showing an image of a refraction room comprising a central screen 82, and tables in the background areas and top vanishing lines defined by slabs on the roof, would not defined an optimized image composition according to the invention at least since being deprived from bottom vanishing lines converging in the direction of the central screen, and neither clues of perception disposed along said vanishing lines.

The FIG. 16 showing a urban landscape with a main centered road delimited by two opposed bottom vanishing lines, a pedestrian walking on the periphery of the road, buildings extending along the vanishing lines and a building seen from the front and wearing a clock 83 would neither correspond to the optimized image according to the invention since being deprived from an object wearing the symbols and incorporated in a realistic way to the scene depicted in the direction of which the vanishing lines would be oriented, and since showing an element supposed to move (walking pedestrian).

As will be easily understood, the features depicted above for appearing on the object (road sign, laptop.) disclosing the symbols testing refraction i.e. the texture, the several symbols, the colorimetry distribution/illustration fitting to the environment scene of the object, can be set on the image picture, and the features depicted above for appearing in the environment of the object (texture, transition element, different types of clues of perspective perception . . . ) can be set on the scene picture.

Otherwise, when the global image including the object and its environment is defined by a unique global picture and no more by superimposed acuity and scene pictures, said features appearing on the object, and in the object's environment will be set on said unique global picture.

The above principles applied to an image shown during a refraction test, can be used to define a video optimized for the same purpose.

In order for the video to be realistic, there has to be characters, and more generally life in the video. In addition, the movements shown to the observer must not be perceived as being too abrupt, at the risk of creating an uncomfortable situation for the patient (acceleration, limited deceleration, etc.) by offering too much image flow. Also, the rotational movements of the camera may be perceived as strange for a patient keeping his gaze fixed, they will therefore be avoided. For the best experience and comfort for the patient, the presence of danger elements (precipice, fire, weapon, car accident, explosion . . . ) will be avoided in the video.

For example, an appropriate video would involve a sequence of images wherein the observer is sitting in a car as depicted on the FIGS. 9 and 10, driving on a straight road with the presence of pedestrians on the sidewalks animated with slow movement (for example walking or eating an ice-cream), the succession of images comprising at least a group of images fulfilling the above mentioned criteria to define a realistic scene to determine refraction, used when testing the vision/level of comfort.

For example, such a video could simulate the wearing of sunglasses to make the subject simulate the relief brought by such equipment.

First of all, the patient must initially understand that he/she is in a very bright environment. To show this addition of light, it is worth moving from a dark to a brighter place. For example, the sequence of images can define for the observer driving a car driven on a road initially in the shade of a line of buildings and suddenly when the line of buildings ends, the sun is beating down on the car and dazzle the observer. This can be combined with an increase in the light level of the backlight of the scene and preferably the acuity screen.

In order to show to the patient the benefit of wearing corrective sun lenses, it is better to show vision loss rather than vision gain. Therefore, the sequence of image shown during the experience, needs to show at first to the patient the vision he/she would have with his corrective sunglasses (with the appropriate corrective power applied on the tunable lenses of the phoropter) and with the colorimetry distribution and shadow/reflection elements corresponding to a vision with sunglasses with correction, then in a second step with the same lighting conditions with sunglasses but without correction, to cancel the correction brought by the phoropter lens (zero power of correction or a power correction equivalent to a former equipment of the subject).

Here is a summary of an example video scenario for a sightseeing sunglass experience that could be built from a sequence of images among which at least a group of images fulfills the above requirements.

The patient is in a driving situation in a bright environment (very sunny road) and wears corrected polarized sunglasses (the correction being brought by the phoropter or the successive images being clear). He stops at a stop sign, reads the license plate and other information on panels, and then his corrective sunglasses are removed (cancellation of the correction brought by the phoropter or increase in the blur level of the successive images corresponding to the correction need of the subject and generation of a bright environment). He can no longer read the information he read previously. The car restarts, there are a lot of reflections on the sea, on the windows of buildings and the windshields of cars, and the light is strong. The car pulls into a parking lot at the end of the road, his corrective sunglasses are put back on (comfortable lighting conditions and correction brought by the phoropter or retrieval of clear images) and he can again see what is written on a banner pulled by an airplane, on the ice cream parlor's sign, on the menu card of a restaurant, while it was difficult without his glasses.

The invention concerns in addition to the embodiment of the FIG. 4 dedicated to bright light conditions, an optometry device dedicated to the testing of refraction at low luminance conditions, more specifically dark or night conditions.

Indeed, during a traditional visual examination, the measurements are carried out in a high luminance environment. But this environment is not representative of all the conditions that the visual system may face. In fact, it has been observed that in low luminance conditions the visual system adapts to maintain a certain performance. In a low luminance environment the pupil dilates, aberrations tend to increase and accommodation is modified. It has been reported by several authors a phenomenon of nocturnal myopia, which causes reduced vision in users and is the cause of complaints of discomfort at night.

To implement such low luminance examination, certain constraints must be taken into account, such as reducing the brightness of the examination room, the time to adapt to darkness, and the number of sources of parasitic light that may interfere with the smooth running of the examination (e.g. computer screen light for example). Controlling the light environment of the examination room is a major issue in the successful assessment of subject complaints and the determination of refraction in nighttime conditions. This would allow professionals to assess the visual abilities of subjects in low-luminance conditions in order to provide them with equipment suited to their needs and complaints.

The optometry device and method according to the invention, aims at solving these issues specifically into optometry devices combining virtually two images defining a superimposition zone between each other, into which a contrast decrease occurs.

To this end, the combined image resulting from the virtual merge of the scene image and the visual test image is provided with a uniform colorimetry distribution with a low luminance level (lower than 100 cd/m$^2$, preferably lower than cd/m$^2$, more preferably lower than 30 cd/m$^2$) thanks to the control unit that controls both visual test and scene pictures colorimetry distributions dependently one another to define a night driving and uniform light condition for the combined image.

Thus, the brightness of both screens are adapted according to the condition tested:

For day light testing conditions (FIG. 4) the scene and acuity screens 21, 22 luminances are both set to more than 40%, preferably 50%, for example 50%.

For night testing conditions (FIG. 16) the scene and acuity screens 21, 22 luminances are both set below 30%, preferably below 20%, more preferably below 10%, even more preferably below 5% for example 1%.

For example, as depicted on the FIG. 16, the scene picture providing the scene image is controlled by the control unit to display a background urban landscape seen at night with lit street lights and seen from the inside of a car from the point of view of the driver, a steering wheel of which being noticeable. The average luminance of this picture is fixed to have a low luminance level (lower than 100 cd/$m^2$, preferably lower than 50 cd/$m^2$, more preferably lower than 30 cd/$m^2$).

Also, the acuity picture providing the acuity image is controlled by the control unit to display visual test image in the form of a dark road panel with letters with an average luminance fixed in the same range as the scene picture i.e. respectively to have a low luminance level (lower than 100 cd/$m^2$, preferably lower than 50 cd/$m^2$, more preferably lower than 30 cd/$m^2$.

Moreover in the scene picture, the scene zone implying transparency for the corresponding virtual scene image and in the superimposition area between the visual test image and the scene image, is set with a low level of color in the RGB color model, i.e. RGB triplet values being each, below 40, more preferably below more preferably below 20, more preferably below 10, more preferably below 5 and more preferably at zero, out of 255. For example the RGB triplet of the zone implying transparency of the scene picture is set to (0, 0, 0) resulting in black or pure black color. The use of such colorimetry distribution allows to avoid any remaining color appearing on the superimposition zone of the acuity and scene images or any contrast decrease.

A color in the RGB color model is described by indicating how much of each of the red, green, and blue is included. The color is expressed as an RGB triplet (r,g,b), each component of which can vary from zero to a defined maximum value. If all the components are at zero the result is black; if all are at maximum, the result is the brightest representable white.

These ranges may be quantified in several different ways:

From 0 to 1, with any fractional value in between. This representation is used in theoretical analyses, and in systems that use floating point representations.

Each color component value can also be written as a percentage, from 0% to 100%.

In computers, the component values are often stored as unsigned integer numbers in the range 0 to 255, the range that a single 8-bit byte can offer. These are often represented as either decimal or hexadecimal numbers.

High-end digital image equipment are often able to deal with larger integer ranges for each primary color, such as 0 . . . 1023 (10 bits), 0 . . . 65535 (16 bits) or even larger, by extending the 24-bits (three 8-bit values) to 32-bit, 48-bit, or 64-bit units (more or less independent from the particular computer's word size). FIGS. 20*a*-20*d* depicts pictures possibly displayed by the scene screen (shown here without the black rectangle constituting the zone implying transparency) illustrating light condition evolution between day (FIG. 20*a*) and night (FIG. 20*d*) through dust (FIG. 20*b*) and dark (FIG. 20*c*).

These images could be used either combined with acuity pictures with corresponding luminance, and providing the screen picture comprises also a corresponding zone implying transparency.

Or be used as they are represented, in the same order in a video aiming at putting the subject into decreasing lighting exposure during a certain period of time to render more pleasant and therefore perceived shorter in time a 5 or 10 minutes transition phase between a first phase of the examination dedicated to day-light conditions, and a second phase dedicated to night conditions. This transition phase can be accompanied by corresponding relaxing sounds such as music, natural sounds.

The speed of decrease of the luminance level can be fixed at a predetermined value comfortable for the subject.

For example the disclosed four pictures are displayed in 12 s and figure begins with a luminance of more than 50 cd/$m^2$ for example 60 cd/$m^2$ and figure at a luminance below 10 cd/$m^2$ such as 1 cd/$m^2$.

Furthermore, the optometry device according to the invention can disclose in the pictures displayed by the scene screen and/or provide directly or indirectly, additional lighting spots imitating the kind of disturbing lights encountered at night (moon light, street lights, headlights of cars traveling in the opposite direction as disclosed in the FIG. 16 and/or reflecting in the side or inner rear mirror of a car . . . ) so as to test the level of discomfort subject or the performance reached by a specific correction brought by the refraction unit.

In a not illustrated embodiment, such light source can be brought by a specific light source as a LED, fixed inside the casing (either fixed on the scene screen around the picture displayed by the scene screen, or fixed on an inner wall of the casing on the optical path seen by the observer directly or further to a reflection on a mirror or beam splitter).

Moreover, to avoid disturbing reflection to occur on the main face of the visual test screen (21) and/or the scene screen (22), one or both of them is/are provided with an anti-reflective coating). For example, these coating can be constituted by any kind of film providing an anti-glare or anti-reflective effect, such as a multilayer structure of high index and low index alternating material layers, a mattified coating, a metalized coating or a coating provided with an electroplate treatment, with the aim of bringing an additional roughness to the external screen main face that reduces its brightness and therefore contributes to maintaining the contrast of the picture displayed and therefor of the combined image obtained from the scene and acuity images of corresponding screens.

And to isolate the subject from parasite lighting exposure coming from the examining room, the optometry device can be provided with a light isolating device as illustrated on the FIGS. 17*a*, 17*b* that includes a flexible mask aiming at conforming with at least part of the subject's face and surrounding the subject's eyes, and a rigid junction part connecting the flexible mask to a head support of the refraction test unit, More precisely, as shown on the FIG. 18 the flexible mask has global cylindrical or truncated shape with a rear larger edge defining a large upper recess aiming at receiving the brow of the individual, and a smaller bottom recess aiming at receiving the subject's nose, and side walls aiming at following the subject's side faces. The opposite smaller front edge aims at being fixed to the rear side of the refraction unit surrounding the exit apertures.

The rigid junction part of the light isolating device as illustrated on the FIG. 19, has a longitudinal shape aiming at following the front upper edge of the flexible mask and to be fixed to the latter by its rear main face, and to be fixed to a head support of the refraction unit by its front face.

To allow an easy, simple and fast method of manufacture of the light isolating device, its constitution is made in two separate parts, one flexible and possibly standard, the second rigid and able to be 3D-printed and therefore with any shape allowing to define an interface on demand between any flexible mask, and any head support of any refraction unit.

Another option to decrease lighting parasite, is to use, for the keyboard and interface controlling the optometry device at the disposition of the expert testing the subject, to use a "night mode" in which the keyboard/mouse would have no back lighting, and the digital interface would have a dark background and slightly bright letters as the one of a GPS device set in night mode.

The invention claimed is:

1. An optometry device for testing an individual's eye, comprising:

a refraction test unit having a vision correction optical system for providing different vision correction power values; and a display unit comprising:

a projection optical system adapted to produce from a scene picture and from a visual test picture including a functional zone, respectively:

a scene image produced along a scene optical path of said projection optical system at a scene distance from the individual's eye; and a visual test image produced along a visual test optical path of said projection optical system at a visual test distance from the individual's eye smaller than or equal to said scene distance of projection, said visual test image being superimposed at least partially with said scene image, said visual test image being configured to test the individual's vision and comprising at least one optotype or symbol; and at least one control unit adapted to control said projection optical system, wherein said at least one control unit is configured to define in the scene picture at least one scene zone providing transparency for a corresponding virtual scene image by having a reduced luminance relative to the other parts of the scene picture and to reduce luminance of said at least one scene zone in the superimposition area between the visual test image and the scene image, allowing the individual's eye to observe the functional zone of the visual test image without contrast decrease, at the visual test distance, and said visual test distance is modifiable and said at least one control unit is configured to define in the visual test picture one frame providing transparency for the corresponding virtual visual test image, surrounding the functional zone of the visual test picture, wherein frame shape features are modified based on said visual test distance so that the functional zone of the visual test image has a shape and an aspect ratio substantially identical for different visual test distances.

2. The optometry device according to claim 1, wherein said at least one scene zone providing transparency is configured by the control unit to have a predetermined colorimetry distribution compared to the remaining parts of said scene picture, said predetermined colorimetry distribution of the at least one scene zone providing transparency being configured by the control unit to have a luminance lower than 100 cd/m$^2$.

3. The optometry device according to claim 1, wherein a predetermined colorimetry distribution of the at least one scene zone providing transparency is configured by the control unit to have a color in the RGB color model whose each component is below 40.

4. The optometry device according to claim 1, wherein the at least one control unit drives the projection optical system so that a peripheral zone of said scene zone providing transparency is fuzzy.

5. The optometry device according to claim 1, wherein said visual test distance is modifiable, and wherein said visual test image dimensions changes in function of visual test distance, said at least one control unit being configured to modify the dimensions of the at least one scene zone providing transparency according to the dimensions of the visual test image.

6. The optometry device according to claim 1, wherein the device comprises a flexible mask and a rigid junction part connecting the flexible mask to a head support of the refraction test unit.

7. The optometry device according to claim 6, wherein the junction part is made by additive manufacturing.

8. An apparatus comprising:

a memory configured to store set of pictures comprising a visual test picture and a scene picture useful for an optometry device having a vision correction optical system for providing different vision correction power values for testing an individual's eye, the optometry device including a projection optical system adapted to produce from corresponding scene picture and corresponding visual test picture including a functional zone, respectively:

a scene image produced along a scene optical path of said projection optical system at a scene distance from the individual's eye; and a visual test image produced along a visual test optical path of said projection optical system at a visual test distance from the individual's eye smaller than or equal to said scene distance of projection, being superimposed at least partially with the scene image, said visual test image being configured to test the individual's vision and comprising at least one optotype or symbol, wherein the scene picture comprises at least one scene zone implying providing transparency for the corresponding virtual scene image by having a reduced luminance relative to the other parts of the scene picture and wherein luminance of said at least one scene zone is reduced in the superimposition area between the visual test image and the scene image allowing the individual's eye to observe the functional zone of the visual test image without contrast decrease at the visual test distance, and wherein the visual test picture comprises a frame providing transparency for the corresponding virtual visual test image, surrounding the functional zone of the visual test picture, wherein frame shape features are modified based on visual test distance so that the functional zone of the visual test image has a shape and an aspect ratio substantially identical for different visual test distances.

9. The apparatus according to claim 8, wherein the scene picture comprises at least two opposed bottom vanishing lines oriented in a direction of said at least one scene zone providing transparency, defining background areas and foreground areas along the vanishing lines, and wherein the functional zone of the visual test picture is defined such that the functional zone appears on the visual test image as being displayed in a vertical plane for the individual.

10. The apparatus according to claim 9, wherein said visual test distance is modifiable at least between a far and a near test distance, and wherein the vanishing lines converge toward a point positioned below the at least one scene zone providing transparency for far test distance, and above or into said at least one scene zone providing transparency for near test distance.

11. The apparatus according to claim 8, wherein the memory is configured to store several visual test pictures and several corresponding scene pictures intended to be displayed successively so as to define a video.

12. The apparatus according to claim 11, wherein the sequence of successive visual test pictures and corresponding scene pictures defines colorimetry and/or luminance evolution so as to provide an observer of the corresponding sequence of images, with a perception of light conditions changing from dark to bright conditions or from bright to dark conditions.

13. A display device comprising: a projection optical system adapted to produce from a scene picture and from a visual test picture including a functional zone, respectively:

a scene image produced along a scene optical path of said projection optical system at a scene distance from the individual's eye; and a visual test image produced along a visual test optical path of said projection optical system at a visual test distance from the individual's eye smaller than or equal to said scene distance of projection, said visual test image being superimposed at least partially with the scene image, said visual test image being configured to test the individual's vision and comprising at least one optotype or symbol; and circuitry configured to control said projection optical system, wherein the circuitry is configured to define in the scene picture at least one scene zone implying providing transparency by having a reduced luminance relative to the other parts of the scene picture and to reduce luminance of said at least one scene zone in the superimposition area between the visual test image and the scene image, allowing the individual's eye to observe the functional zone of the visual test image without contrast decrease, at the visual test distance, and wherein said visual test distance is modifiable and wherein said circuitry is configured to define in the visual test picture one frame providing transparency for the corresponding virtual visual test image, surrounding the functional zone of the visual test picture, wherein frame shape features are modified based on said visual test distance so that the functional zone of the visual test image has a shape and an aspect ratio substantially identical for different visual test distances.

* * * * *